(12) United States Patent
Tehrani et al.

(10) Patent No.: US 7,979,128 B2
(45) Date of Patent: Jul. 12, 2011

(54) DEVICE AND METHOD FOR GRADUALLY CONTROLLING BREATHING

(75) Inventors: Amir J. Tehrani, San Francisco, CA (US); David Ligon, San Francisco, CA (US); Chang Lee, Redwood City, CA (US); Rose Province, San Jose, CA (US); Amy Michelle Goodman, San Francisco, CA (US)

(73) Assignee: RMX, LLC, San Francisco, CA (US)

( * ) Notice: Subject to any disclaimer, the term of this patent is extended or adjusted under 35 U.S.C. 154(b) by 784 days.

(21) Appl. No.: 11/271,264

(22) Filed: Nov. 10, 2005

(65) Prior Publication Data

US 2006/0149334 A1    Jul. 6, 2006

Related U.S. Application Data

(63) Continuation-in-part of application No. 10/966,484, filed on Oct. 15, 2004, now abandoned, and a continuation-in-part of application No. 10/966,474, filed on Oct. 15, 2004, and a continuation-in-part of application No. 10/966,421, filed on Oct. 15, 2004, and a continuation-in-part of application No. 10/966,472, filed on Oct. 15, 2004, each which is a continuation-in-part of application No. 10/686,891, filed on Oct. 15, 2003.

(51) Int. Cl.
*A61N 1/36* (2006.01)

(52) U.S. Cl. ........................................ 607/42

(58) Field of Classification Search .................... 607/42
See application file for complete search history.

(56) References Cited

U.S. PATENT DOCUMENTS

| | | | |
|---|---|---|---|
| 4,827,935 A | 5/1989 | Geddes | |
| 4,830,008 A * | 5/1989 | Meer | 607/42 |
| 5,056,519 A | 10/1991 | Vince | 128/419 |
| 5,146,918 A | 9/1992 | Kallok et al. | 128/419 |
| 5,174,287 A | 12/1992 | Kallok et al. | 128/419 |
| 5,190,036 A | 3/1993 | Linder | |
| 5,211,173 A | 5/1993 | Kallok et al. | 128/419 |
| 5,215,082 A | 6/1993 | Kallok et al. | 128/419 |
| 5,233,983 A | 8/1993 | Markowitz | 607/42 |
| 5,265,604 A | 11/1993 | Vince | 607/42 |
| 5,281,219 A | 1/1994 | Kallok | 607/42 |
| 5,300,094 A | 4/1994 | Kallok et al. | 607/42 |
| 5,423,327 A | 6/1995 | Clauson et al. | 128/716 |
| 5,423,372 A | 6/1995 | Kearney | |

(Continued)

FOREIGN PATENT DOCUMENTS

| | | |
|---|---|---|
| WO | WO 86/00234 | 1/1986 |
| WO | WO/8600234 | 1/1986 |

OTHER PUBLICATIONS

Don D. Sin, Effects of Continuous Positive Airway Pressure on Cardiovascular Outcomes in Heart Failure Patients With and Without Cheyne-Stokes Respiration, *Circulation*, 102:61-66 (Jul. 4, 2000).

(Continued)

*Primary Examiner* — Michael Kahelin
(74) *Attorney, Agent, or Firm* — Levine Bagade Han LLP

(57) ABSTRACT

A device and method is provided for controlling breathing of a subject by electrically stimulating tissue associated with the diaphragm or phrenic nerve of the subject.

16 Claims, 17 Drawing Sheets

U.S. PATENT DOCUMENTS

| | | | |
|---|---|---|---|
| 5,483,969 A | 1/1996 | Testerman et al. | |
| 5,485,851 A | 1/1996 | Erickson | 128/716 |
| 5,522,862 A | 6/1996 | Testerman et al. | 607/42 |
| 5,524,632 A | 6/1996 | Stein et al. | 128/733 |
| 5,540,731 A | 7/1996 | Testerman et al. | 607/42 |
| 5,540,732 A | 7/1996 | Testerman et al. | 607/42 |
| 5,540,733 A | 7/1996 | Testerman et al. | 607/42 |
| 5,546,952 A | 8/1996 | Erickson | |
| 5,549,655 A | 8/1996 | Erickson | |
| 5,572,543 A | 11/1996 | Heinemann et al. | |
| 5,678,535 A | 10/1997 | DiMarco | 128/200.24 |
| 5,766,228 A | 6/1998 | Bonnet et al. | 607/16 |
| 5,797,923 A | 8/1998 | Aiyar et al. | 606/129 |
| 5,800,470 A | 9/1998 | Stein et al. | 607/20 |
| 5,814,086 A | 9/1998 | Hirschberg | |
| 5,830,008 A | 11/1998 | Broschard, III | |
| 5,876,353 A | 3/1999 | Riff | 600/547 |
| 5,895,360 A | 4/1999 | Christopherson et al. | 600/529 |
| 5,911,218 A | 6/1999 | DiMarco | 128/200.24 |
| 5,944,680 A | 8/1999 | Christopherson | |
| 6,021,352 A | 2/2000 | Christopherson et al. | 607/42 |
| 6,099,479 A | 8/2000 | Christopherson et al. | 600/529 |
| 6,212,435 B1 | 4/2001 | Lattner et al. | 607/134 |
| 6,224,562 B1 | 5/2001 | Lurie et al. | 601/41 |
| 6,251,126 B1 | 6/2001 | Ottenhoff et al. | 607/42 |
| 6,269,269 B1 | 7/2001 | Ottenhoff et al. | 607/42 |
| 6,312,399 B1 | 11/2001 | Lurie et al. | |
| 6,314,324 B1 | 11/2001 | Lattner et al. | |
| 6,345,202 B2 | 2/2002 | Richmond et al. | 607/42 |
| 6,415,183 B1 | 7/2002 | Scheiner et al. | 607/42 |
| 6,463,327 B1 | 10/2002 | Lurie | |
| 6,480,733 B1 | 11/2002 | Turcott | 600/516 |
| 6,489,447 B1 | 12/2002 | Basey et al. | |
| 6,512,949 B1 | 1/2003 | Combs et al. | |
| 6,527,729 B1 | 3/2003 | Turcott | 600/528 |
| 6,542,774 B2 | 4/2003 | Hill | |
| 6,572,543 B1 | 6/2003 | Christopherson et al. | 600/300 |
| 6,574,507 B1 | 6/2003 | Bonnet | 607/20 |
| 6,587,726 B2 | 7/2003 | Lurie et al. | |
| 6,589,188 B1 | 7/2003 | Street et al. | 600/538 |
| 6,600,949 B1 | 7/2003 | Turcott | 600/518 |
| 6,633,779 B1 | 10/2003 | Lee et al. | 607/42 |
| 6,651,652 B1 | 11/2003 | Ward | 128/200.24 |
| 6,731,984 B2 | 5/2004 | Cho et al. | 607/17 |
| 6,735,479 B2 | 5/2004 | Fabian et al. | |
| 6,752,765 B1 | 6/2004 | Jensen et al. | 600/536 |
| 6,811,537 B2 | 11/2004 | Bardy | |
| 6,830,548 B2 | 12/2004 | Bonnet et al. | 600/529 |
| 6,881,192 B1 | 4/2005 | Park et al. | |
| 6,908,437 B2 | 6/2005 | Bardy | |
| 7,058,453 B2 | 6/2006 | Nelson et al. | |
| 7,070,568 B1 | 7/2006 | Koh et al. | |
| 7,082,331 B1 | 7/2006 | Park et al. | |
| 7,117,032 B2 | 10/2006 | Childre et al. | |
| 7,277,757 B2 | 10/2007 | Casavant et al. | |
| 7,532,934 B2 | 5/2009 | Lee et al. | |
| 7,840,270 B2 | 11/2010 | Ignagni et al. | |
| 2002/0049482 A1 | 4/2002 | Fabian et al. | 607/60 |
| 2002/0193697 A1 | 12/2002 | Cho et al. | 600/529 |
| 2002/0193839 A1 | 12/2002 | Cho et al. | 607/17 |
| 2003/0127091 A1 | 7/2003 | Chang | |
| 2003/0153953 A1 | 8/2003 | Park et al. | 607/17 |
| 2003/0153954 A1 | 8/2003 | Park et al. | 607/17 |
| 2003/0153955 A1 | 8/2003 | Park et al. | 607/17 |
| 2003/0153956 A1 | 8/2003 | Park et al. | 607/17 |
| 2003/0195571 A1 | 10/2003 | Burnes et al. | 607/9 |
| 2003/0204213 A1 | 10/2003 | Jensen et al. | |
| 2003/0225339 A1 | 12/2003 | Orr et al. | |
| 2004/0059240 A1 | 3/2004 | Cho et al. | |
| 2004/0077953 A1 | 4/2004 | Turcott | 600/483 |
| 2004/0088015 A1 | 5/2004 | Casavant et al. | 607/14 |
| 2004/0111040 A1 | 6/2004 | Ni et al. | 600/534 |
| 2004/0122484 A1 | 6/2004 | Hatlestad et al. | |
| 2004/0134496 A1 | 7/2004 | Cho et al. | 128/204.33 |
| 2004/0138719 A1 | 7/2004 | Cho et al. | 607/42 |
| 2004/0176809 A1 | 9/2004 | Cho et al. | 607/14 |
| 2004/0199221 A1 | 10/2004 | Fabian et al. | |
| 2004/0225226 A1 | 11/2004 | Lehrman et al. | 600/529 |
| 2004/0237963 A1 | 12/2004 | Berthon-Jones | 128/204.26 |
| 2005/0021102 A1* | 1/2005 | Ignagni et al. | 607/42 |
| 2005/0039745 A1 | 2/2005 | Stahmann et al. | |
| 2005/0043644 A1 | 2/2005 | Stahmann et al. | 600/529 |
| 2005/0043772 A1 | 2/2005 | Stahmann et al. | 607/42 |
| 2005/0055060 A1 | 3/2005 | Koh et al. | 607/17 |
| 2005/0061315 A1 | 3/2005 | Lee et al. | 128/204.21 |
| 2005/0061319 A1 | 3/2005 | Hartley et al. | 128/204.18 |
| 2005/0061320 A1 | 3/2005 | Lee et al. | 128/204.18 |
| 2005/0065563 A1 | 3/2005 | Scheiner | 607/9 |
| 2005/0065567 A1 | 3/2005 | Lee et al. | 607/17 |
| 2005/0074741 A1 | 4/2005 | Lee et al. | 434/433 |
| 2005/0076909 A1 | 4/2005 | Stahmann et al. | |
| 2005/0080461 A1 | 4/2005 | Stahmann et al. | 607/17 |
| 2005/0085734 A1 | 4/2005 | Tehrani | |
| 2005/0085865 A1 | 4/2005 | Tehrani | |
| 2005/0085866 A1 | 4/2005 | Tehrani | |
| 2005/0085867 A1 | 4/2005 | Tehrani | |
| 2005/0085868 A1 | 4/2005 | Tehrani | |
| 2005/0085869 A1 | 4/2005 | Tehrani | |
| 2005/0101833 A1 | 5/2005 | Hsu et al. | 600/26 |
| 2005/0107860 A1 | 5/2005 | Ignagni et al. | 607/116 |
| 2005/0115561 A1 | 6/2005 | Stahmann et al. | 128/200.24 |
| 2005/0119711 A1 | 6/2005 | Cho et al. | |
| 2005/0145246 A1 | 7/2005 | Hartley et al. | 128/203.14 |
| 2005/0148897 A1 | 7/2005 | Cho et al. | 600/533 |
| 2005/0165457 A1 | 7/2005 | Benser et al. | |
| 2005/0224076 A1 | 10/2005 | Pfichner et al. | |
| 2005/0240240 A1 | 10/2005 | Park et al. | 607/42 |
| 2005/0261600 A1 | 11/2005 | Aylsworth | |
| 2005/0261747 A1 | 11/2005 | Schuler et al. | |
| 2006/0030894 A1 | 2/2006 | Tehrani | |
| 2006/0036294 A1 | 2/2006 | Tehrani | |
| 2006/0058852 A1 | 3/2006 | Koh et al. | |
| 2006/0064030 A1 | 3/2006 | Cosentino et al. | |
| 2006/0064325 A1 | 3/2006 | Matsumoto et al. | |
| 2006/0122622 A1 | 6/2006 | Truckai et al. | |
| 2006/0122661 A1 | 6/2006 | Mandell | |
| 2006/0122662 A1 | 6/2006 | Tehrani et al. | |
| 2006/0142815 A1 | 6/2006 | Tehrani et al. | |
| 2006/0149334 A1 | 7/2006 | Tehrani et al. | |
| 2006/0155341 A1 | 7/2006 | Tehrani et al. | |
| 2006/0167523 A1 | 7/2006 | Tehrani et al. | |
| 2006/0190052 A1 | 8/2006 | Yun | |
| 2006/0224211 A1 | 10/2006 | Durand et al. | |
| 2006/0247729 A1 | 11/2006 | Tehrani et al. | |
| 2006/0282131 A1 | 12/2006 | Caparso | |
| 2007/0021795 A1 | 1/2007 | Tehrani | |
| 2008/0177347 A1 | 7/2008 | Tehrani et al. | |
| 2008/0188903 A1 | 8/2008 | Tehrani et al. | |

OTHER PUBLICATIONS

Takaomi Taira, M.D., Ph.D., et. al, Phrenic Nerve Stimulation for Diaphragm Pacing With a Spinal Cord Stimulator, *Surg Neurol*, 59:128-132 (2003).

Donald B. Shaul, et. al, Thoracoscopic Placement of Phrenic Nerve Electrodes for Diaphragmatic Pacing in Children, *Journal of Pediatric Surgery*, 37:974-978 (Jul. 2002).

Christopher Reeve, New Implantable Breathing Device, *University Hospitals of Cleveland*, pp. 1-4, (2003).

Christopher Reeve, Christopher Reeve Paralysis Foundation Questions & Answers, pp. 1-3 (Mar. 13, 2003).

T. Mitsuyana, et. al, Diaphragm Pacing With the Spinal Cord Stimulator, *Aeta Neurochir*, 87:89-92 (2003).

Harish Aiyar, et. al, Laparoscopic Implant Device for Intermuscular Electrodes, IEEE-EMBC and CMBCC, pp. 1167-1168, ((1995).

Harish Aiyar,et.al, Laparoscopic Implant Instrument for the Placement of Intramuscular Electrodes in the Diaphragm, *Transactions on Rehabilitation Engineering*, pp. 360-371 (Sep. 1999).

Anthony F. DiMarco, et. al, Phrenic Nerve Pacing in a Tetraplegic Patient via Intramuscula Diaphragm Electrodes,*American Journal of Respiratory and Critical Care Medicine*, 144:1604-1606 (2002).

S.Sauermann, et. al, Computer Aided Adjustment of the Phrenic Pacemaker: Automatic Functions, Documentation, and Quality Control, *Artificial Organs*, 21(3):216-218 (1997).

B.D. Schmit, et. al, An Implantable Impedance Pneumograph Monitor for Detection of Diaphragm Contraction and Airway Obstruction During Diaphragm Pacing, *Medical & Biological Engineering & Computing*, 37:162-168 (1999).

Brian D. Schmit, et. al, Laparoscopic Placement of Electrodes for Diaphragm Pacing Using Stimulation to Locate the Phrenic Nerve Motor Points, *Transactions on Rehabilitation Engineering*, 6(4):382-390 (Dec. 1998).

M. Noshiro, et al., Method of Electrophrenic Respiration for Producing a Natural Respiratory Flow Rate Using Feedback Control of Tidal Volume Waveform, *Med. & Bio. Eng. & Comput.*, 20:765-771, (Nov. 1982).

W. Glenn "Diaphragm Pacing: Present Status" PACE vol. 1 p. 357-370 (1978).

R. Heinzer et al "Lung Volume and Continuous Positive Airway Pressure Requirements in Obstructive Sleep Apnea" Am J. Resp Crit Care Med vol. 172 p. 114-117 (Apr. 2005).

A Jensen et al. Signal Transduction in Smooth Muscle: Airway caliber in healthy and asthmatic subjects effects of bronchial challenge and deep inspirations. J. Appl Physiol 91: 506-515 (2001).

W. Glenn et al: "Diaphragm Pacing" Journal of Thoracic and Cardiovascular Surgery vol. 75 No. 2, 273-281 (1978).

Patroniti M.D., et al "Sigh Improves Gas Exchange and Lung Volume in Patients with Acute Respiratory Distress Syndrome Undergoing Pressure Support Ventilation" Anesthesiology 96: 788-94 (2002).

P. Simon et al "Vagal Feedback in the Entrainment of Respiration to Mechanical Ventilation in Sleep ing Humans" J. App. Physiol 89: 760-769 (2000).

R. Gosselink Controlled Breathing and Dyspnea in Patients With Chronic Obstructive Pulmonary Disease. Journal of Rehabilitaiton Research and Development vol. 40, No. 5 , Supplement 2 p. 20-34 (Sep./Oct. 2003).

F. Series et al "Increasing the Functional Residual Capacity May Reverse Obstructive Sleep Apnea" Sleep 11(4): 349-353 (1988).

U.S. Appl. No. 11/271,554, filed Nov. 10, 2005 in the name of Tehrani et al., final Office Action mailed Jan. 31, 2011.

U.S. Appl. No. 11/526,949, filed Sep. 25, 2006 in the name of Tehrani, non-final Office Action mailed Oct. 5, 2010.

U.S. Appl. No. 11/981,342, filed Oct. 31, 2007 in the name of Tehrani et al., final Office Action mailed Oct. 7, 2010.

U.S. Appl. No. 11/981,800, filed Oct. 31, 2007 in the name of Tehrani et al., final Office Action mailed Jan. 20, 2011.

U.S. Appl. No. 10/966,421, filed Apr. 8, 2008 in the name of Tehrani, final Office Action mailed Feb. 17, 2011.

Aiyar, H. et al, "Laparoscopic Implant Device for Intermuscular Electrodes," *IEEE-EMBC and CMBCC*, pp. 1167-1168, 1995.

Aiyar, H. et al, "Laparoscopic Implant Instrument for the Placement of Intramuscular Electrodes in the Diaphragm," *Transactions on Rehabilitation Engineering*, pp. 360-371, Sep. 1999.

Bernardi, L. et al, "Effect of Rosary Prayer and Yoga Mantras on Autonomic Cardiovascular Rhythms: Comparative Study," *BMJ*, 323:22-29, Dec. 2001.

Bernardi, L. et al, "Slow Breathing Increases Arterial Baroreflex sensitivity in Patients with Chronic Heart Failure," *Circulation*,2002.

DiMarco, A. F. et al, "Phrenic Nerve Pacing in a Tetraplegic Patient via Intramuscular Diaphragm Electrodes," *American Journal of Respiratory and Critical Care Medicine*, 144:1604-1606, 2002.

Glenn, W. W. L., "Diaphragm Pacing: Present Status," *PACE*, 1: 357-370, Jul.-Sep. 1978.

Gosselink, R. "Controlled Breathing and Dyspnea in Patients With Chronic Obstructive Pulmonary Disease," *Journal of Rehabilitaiton Research and Development*, 40(5)1:20-34, Supplement 2, Sep./Oct. 2003.

Harish, A. et al, "Laparoscoptc Implant Device for Intermuscular Electrodes," *IEEE-EMBC and CMBECC*, pp. 1167-1168, 1995.

Jensen, A. et al, "Signal Transduction in Smooth Muscle: Airway caliber in healthy and asthmatic subjects effects of bronchial challenge and deep inspirations," *J. Appl Physiol*, 91:506-515, 2001.

Mitsuyana, T. et al, "Diaphragm Pacing With the Spinal Cord Stimulator," *Aeta Neurochir*, 87:89-92, 2003.

Noshiro, M. et al., "Method of Electrophrenic Respiration for Producing a National Respiratory Flow Rate Using Feedback Control of Tidal Volume Waveform," *Med. & Bio. Eng. & Comput.*, 20:765-77, Nov. 1982.

Patroniti, M.D., et al "Sigh Improves Gas Exchange and Lung Volume in Patients with Acute Respiratory Distress Syndrome Undergoing Pressure Support Ventilation," *Anesthesiology*,96:788-794, 2002.

Reeve, C., "New Implantable Breathing Device," University Hospitals of Cleveland, pp. 1-4, 2003.

Reeve, C., Christopher Reeve Paralysis Foundation Questions & Answers, pp. 1-3, Mar. 13, 2003.

Sauermann, S. et al, "Computer Aided Adjustment of the Phrenic Pacemaker: Automatic Functions. Documentation, and Quality Control," *Artificial Organs*, 21(3):216-218, 1997.

Schmit, B. D. et al, "Laparoscopic Placement of Electrodes for Diaphragm Pacing Using Stimulation to Locate the Phrenic Nerve Motor Points," *Transactions on Rehabilitation Engineering*, 6(4):382-390, Dec. 1998.

Schmit, B.D. et al, "An Implantable Impedance Pneumograph Monitor for Detection of Diaphragm Contraction and Airway Obstruction During Diaphragm Pacing," *Medical & Biological Engineering & Computing*, 37:162-168, 1999.

Series, F. et al, "Increasing the Functional Residual Capacity May Reverse Obstructive Sleep Apnea Sleep," 11(4):349-353, 1988.

Shaul, D.B. et al, "Thoracoscopic Placement of Phrenic Nerve Electrodes for Diaphragmatic Pacing in Children," *Journal of Pediatric Surgery*, 37:974-978, Jul. 2002.

Shier, D. et al, *Hole's Human Anatomy & Physiology*, pp. 798 (2 pages total).

Simon, P. et al, "Vagal Feedback in the Entrainment of Respiration to Mechanical Ventilation in Sleeping Humans," *J. App. Physiol*, 89:760.769, 2000.

Sin, D. "Effects of Continuous Positive Airway Pressure on Cardiovascular Outcomes in Heart Failure Patients With and Without Cheyne-Stokes Respiration," *Circulation*, 102:61-66, Jul. 4, 2000.

Taira, T. et al, "Phrenic Nerve Stimulation for Diaphragm Pacing With a Spinal Cord Stimulator," *Surg Neurol*. 59:128-132, 2003.

U.S. Appl. No. 10/686,891, filed Oct. 15, 2003 in the name of Tehrani, Non-final Office Action mailed Sep. 18, 2009.

U.S. Appl. No. 11/246,439, filed Oct. 11, 2005 in the name of Tehrani, Non-final Office Action mailed Sep. 30, 2009.

U.S. Appl. No. 11/249,718, filed Oct. 13, 2005 in the name of Tehrani, Non-final Office Action mailed Apr. 18, 2008.

U.S. Appl. No. 11/249,718, filed Oct. 13, 2005 in the name of Tehrani, Final Office Action mailed Apr. 1, 2009.

U.S. Appl. No. 11/249,718, filed Oct. 13, 2005 in the name of Tehrani, Non-final Office Action mailed Nov. 25, 2009.

U.S. Appl. No. 11/981,800, filed Oct. 31, 2007 in the name of Tehrani et al., Non-final Office Action mailed Oct. 7, 2009.

U.S. Appl. No. 10/966,421, filed Oct. 15, 2004 in the name of Tehrani, Final Office Action mailed Oct. 26, 2009.

U.S. Appl. No. 11/271,554, filed Nov. 10, 2005 in the name of Tehrani et al., Non-final Office Action mailed Dec. 24, 2009.

U.S. Appl. No. 11/981,831, filed Oct. 31, 2007 in the name of Tehrani et al., Non-final Office Action mailed Jan. 6, 2010.

U.S. Appl. No. 10/966,474, filed Oct. 15, 2004 in the name of Tehrani, Final Office Action mailed Jan. 21, 2010.

U.S. Appl. No. 10/966,472, filed Oct. 15, 2004 in the name of Tehrani et al., Non-final Office Action mailed Feb. 23, 2010.

U.S. Appl. No. 11/526,949, filed Sep. 25, 2006 in the name of Tehrani, Final Office Action mailed Mar. 19, 2010.

U.S. Appl. No. 11/271,726, filed Nov. 10, 2005 in the name of Tehrani et al., Non-final Office Action mailed Mar. 31, 2010.

U.S. Appl. No. 11/271,315, filed Nov. 10, 2005 in the name of Tehrani et al., Final Office Action mailed Mar. 31, 2010.

U.S. Appl. No. 11/271,315, filed Nov. 10, 2005 in the name of Tehrani et al., Non-final Office Action mailed Oct. 3, 2008.

U.S. Appl. No. 11/981,342, filed Oct. 31, 2007 in the name of Tehrani et al., Non-final Office Action mailed Apr. 15, 2010.

U.S. Appl. No. 11/480,074, filed Jun. 29, 2006 in the name of Tehrani et al., Final Office Action mailed Apr. 30, 2010.

U.S. Appl. No. 10/966,421, filed Oct. 15, 2004 in the name of Tehrani, non-final Office Action mailed Jun. 9, 2010.

U.S. Appl. No. 12/080,133, filed Apr. 1, 2008 in the name of Tehrani et al., non-final Office Action mailed Jun. 10, 2010.

U.S. Appl. No. 11/246,439, filed Oct. 11, 2005 in the name of Tehrani, final Office Action mailed Jun. 29, 2010.

U.S. Appl. No. 11/249,718, filed Oct. 13, 2005 in the name of Tehrani, final Office Action mailed Sep. 14, 2010.

U.S. Appl. No. 10/686,891, filed Oct. 15, 2003 in the name of Tehrani, final Office Action mailed Sep. 15, 2010.

Iazzo, P. ed., "Handbook of Cardiac Anatomy, Physiology, and Devices", p. 398, 2009.

Liem, L.B., "EP 101: Ventricular Tachycardia", EP Lab Digest, v.7, No. 8, Aug. 2007.

Malkin R. et al., "The Effect of Inducing Ventricular Fibrillation with 50-Hz Pacing Versus T are Stimulation on the Ability to Defibrillate", Pacing and Clinical Electrophysiology, vol. 21, issue 5, May 1998.

U.S. Appl. No. 11/480,074, filed Jun. 29, 2006 in the name of Tehrani et al., non-final Office Action mailed Mar. 16, 2011.

U.S. Appl. No. 10/686,891, filed Oct. 15, 2003 in the name of Tehrani, non-final Office Action mailed Mar. 30, 2011.

U.S. Appl. No. 10/966,474, filed Oct. 15, 2004 in the name of Tehrani et al., non-final Office Action mailed Mar. 30, 2011.

U.S. Appl. No. 11/981,727, filed Oct. 31, 2007 in the name of Tehrani et al., non-final Office Action mailed Apr. 4, 2011.

U.S. Appl. No. 11/249,718, filed Oct. 13, 2005 in the name of Tehrani, non-final Office Action mailed Apr. 1, 2011.

U.S. Appl. No. 11/271,726, filed Nov. 10, 2005 in the name of Tehrani et al., non-final Office Action mailed Apr. 4, 2011.

Heinzer, R., et al, "Lung Volume and Continuous Positive Airway Pressure Requirements in Obstructive Sleep Apeau" *American Journal of Respiratory and Critical Care Medicine*, vol. 172, pp. 114-117, 2005.

DiMarco, A F., "Combined Intercostal and Diaphragm Pacing to Provide Artificial Ventilation in Patients With Tetraplegia" *Arch Phys Med Rehabil*, vol. (86), pp. 1200-1207, 2005.

Dunn, R., "Diaphragm and Accessory Respiratory Muscle Stimulation Using Intramuscular Electrodes" *Arch Phys Med Rehabil*, vol. (76), pp. 266-271, 1995.

Glenn, W., et al. "Diaphragm Pacing " *Journal of Thoracic and Cardiovascular Surgery*, vol. (75):2, pp. 273-281, 1978.

\* cited by examiner

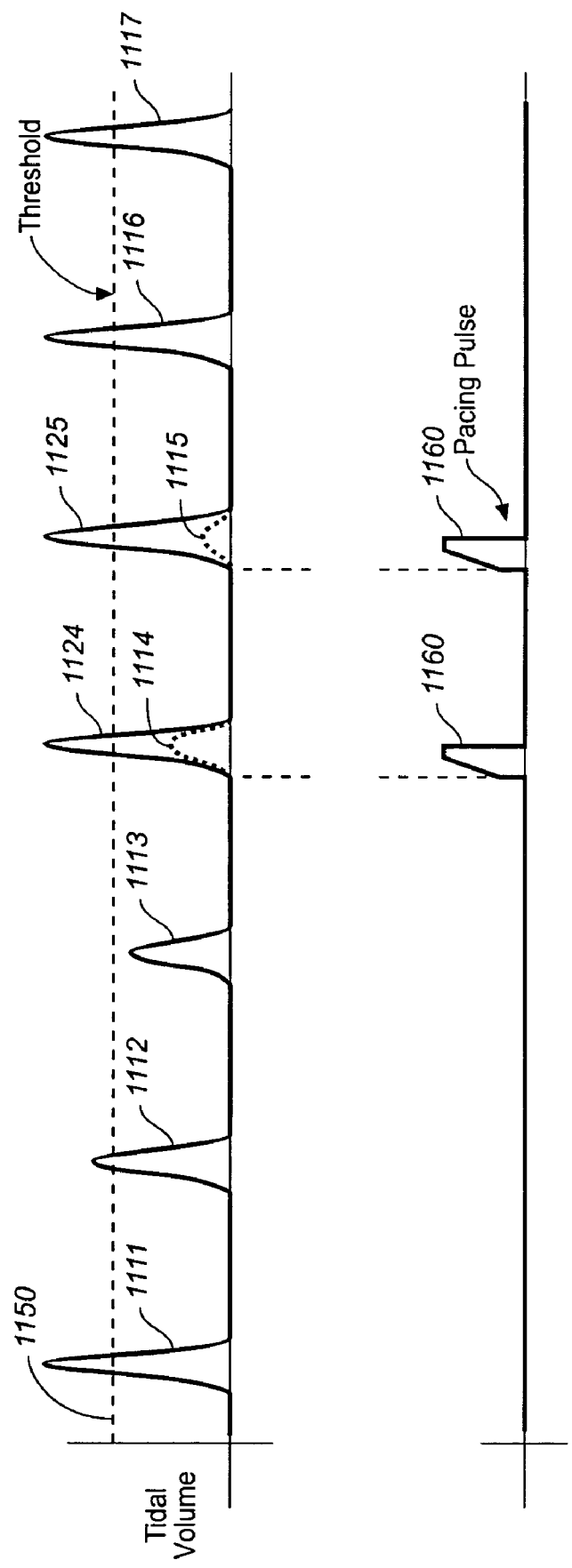

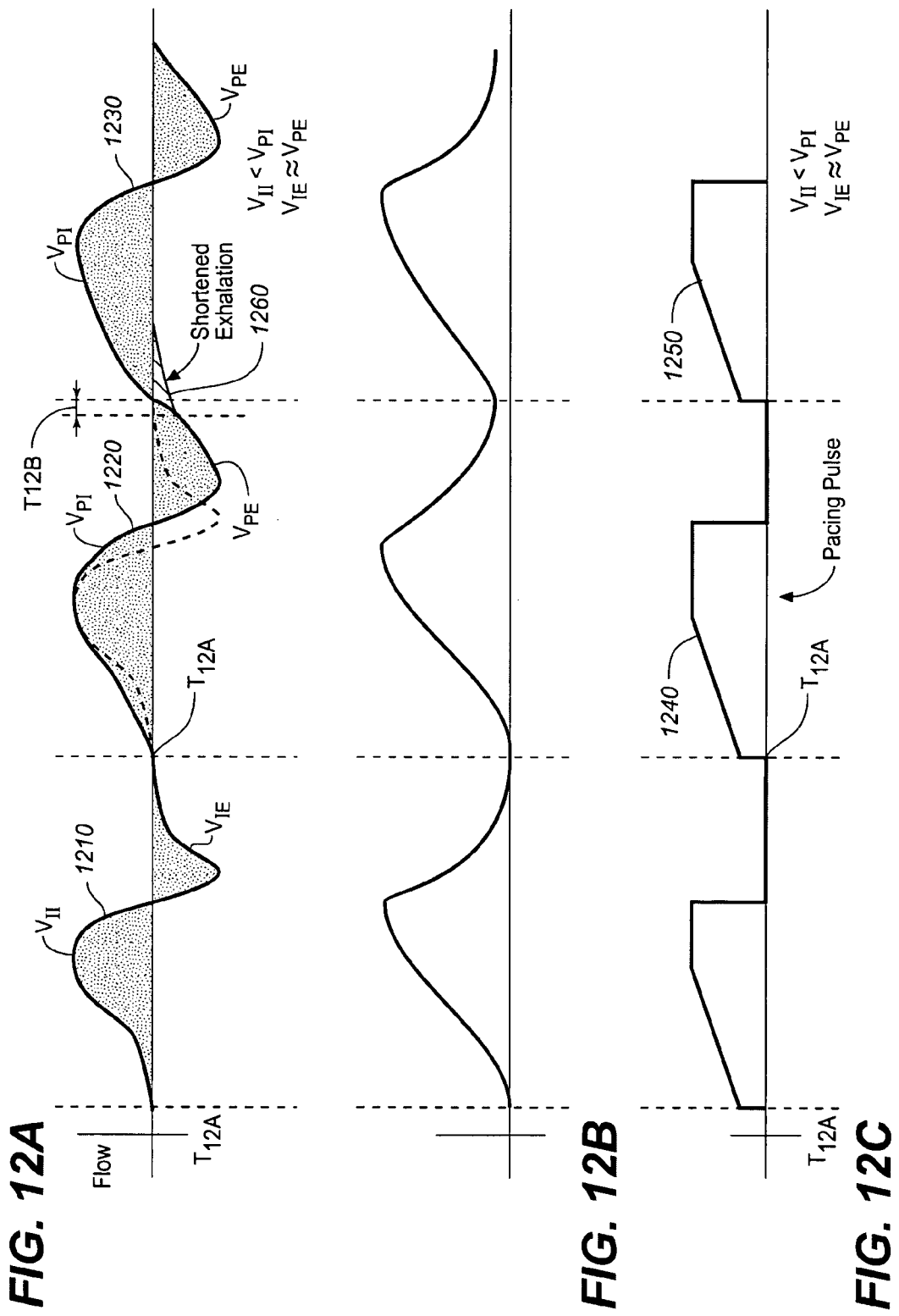

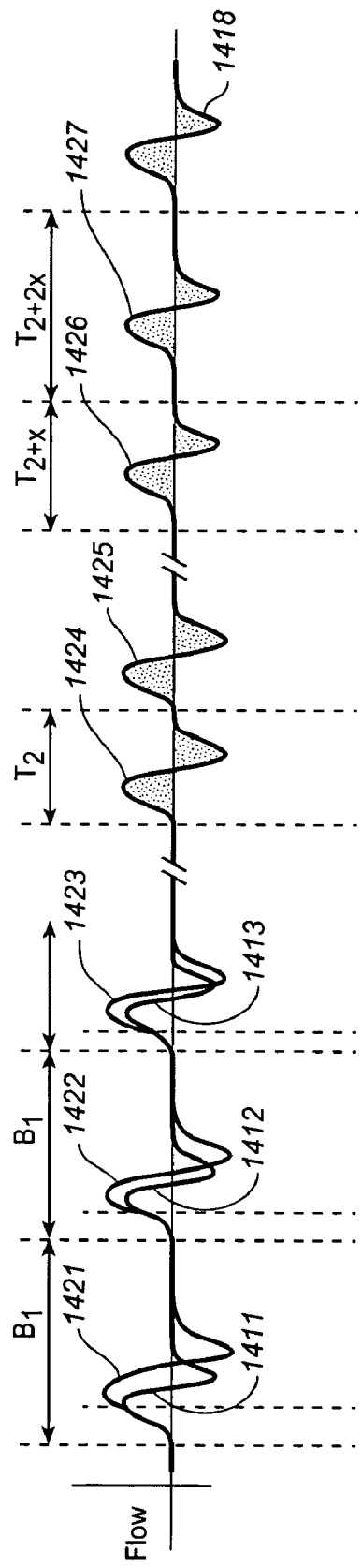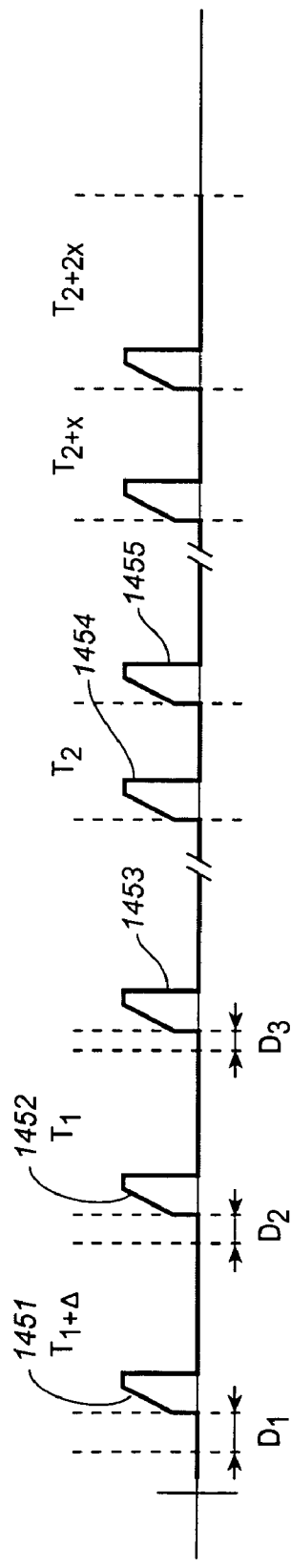
FIG. 14A
FIG. 14B

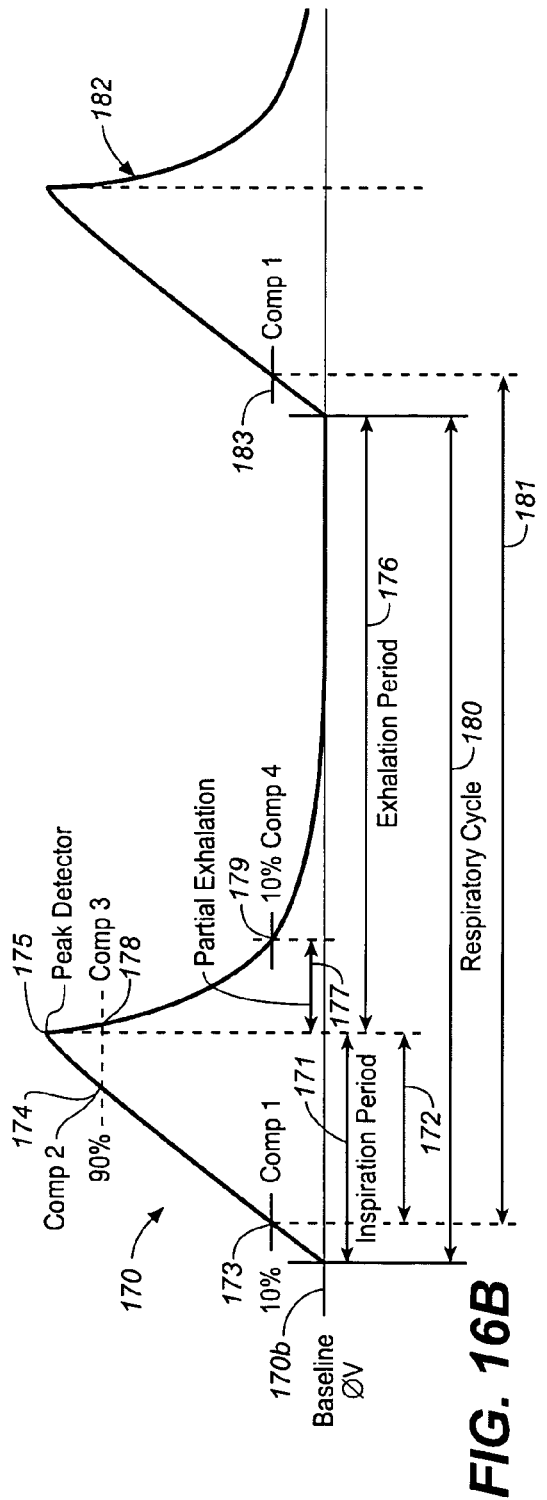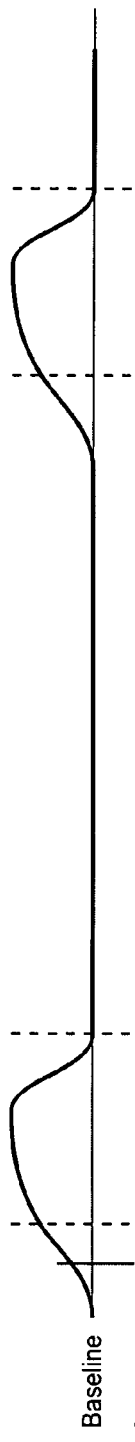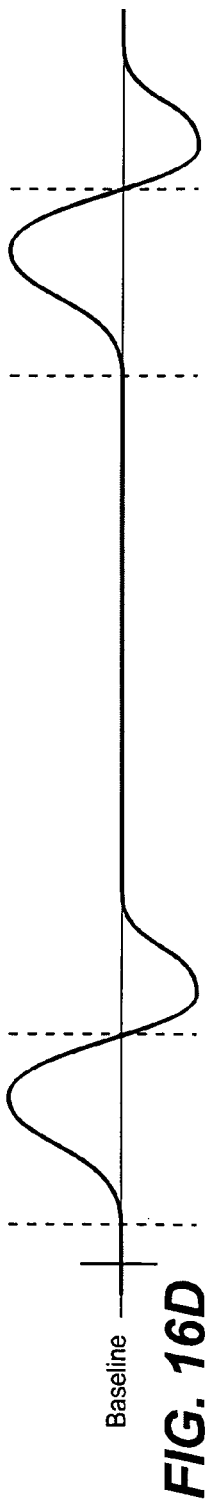

DEVICE AND METHOD FOR GRADUALLY CONTROLLING BREATHING

RELATED APPLICATION DATA

This application is a continuation in part of U.S. application Ser. No. 10/966,484 filed Oct. 15, 2004 (US Pat. Pub. 2005/0085869, now abandoned); U.S. application Ser. No. 10/966,474, filed Oct. 15, 2004 (US Pat. Pub. 2005/0085868); U.S. application Ser. No. 10/966,421, filed Oct. 15, 2004 (US Pat. Pub. 2005/0085866); and U.S. application Ser. No. 10/966,472 filed Oct. 15, 2004 (US Pat. Pub. 2005/0085867) which are continuations in part of U.S. application Ser. No. 10/686,891 filed Oct. 15, 2003 (US Pat. Pub. 2005/0085865) entitled: BREATHING DISORDER DETECTION AND THERAPY DELIVERY DEVICE AND METHOD.

FIELD OF THE INVENTION

This invention relates to a device and method for treating respiratory and related disorders.

BACKGROUND OF THE INVENTION

There are several factors believed to contribute to the occurrence of obstructive respiratory events including anatomical deficiencies, deformities or conditions that increase the likelihood or occurrence of upper airway collapse; ventilatory instability; and fluctuations in lung volumes. There is believed to be a relationship between lung volume and the aperture of the upper airway with larger lung volume leading to greater upper airway patency.

Some obstructive sleep apnea (OSA) patients have increased upper airway resistance and collapsibility that may contribute to vulnerability to obstructive respiratory events. The pharyngeal airway is not supported by bone or cartilignenous structure and accordingly relies on contraction of the upper airway dilator muscles to maintain patency. The pharyngeal airway represents a primary site of upper airway closure.

Some OSA therapy has been based on a belief that OSA results from the size and shape of the upper airway muscles or conditions such as obesity that create a narrowing of the upper air passageway and a resulting propensity for its collapse.

In patients with obstructive sleep apnea, various treatment methods and devices have been used with very limited success.

CPAP machines have been used to control obstructive sleep apnea by creating a continuous positive airway pressure (CPAP) at night. External ventilatory control has been proposed including sensors that sense a cessation of breathing to determine when an obstructive sleep apnea event is occurring.

An implantable stimulator that stimulates the hypoglossal nerve after sensing an episode of obstructive sleep apnea has been proposed but has failed to provide satisfactory results in OSA patients.

Treating OSA has primarily relied on continuous treatment or detection of an obstructive respiratory event when it is occurring, i.e., when the upper air passageway has closed.

Drug therapy has not provided satisfactory results.

In central sleep apnea, as opposed to obstructive sleep apnea, it has been proposed to stimulate a patient's diaphragm or phrenic nerve to induce breathing where there is a lack of central respiratory drive. However, such therapy has be contraindicated for obstructive sleep apnea or respiratory events where there is an obstructive component, at least in part because stimulating a patient to breathe when the airway is obstructed is believed to further exacerbate the collapsing of the airway passage by creating a pressure that further closes the airway.

Accordingly, it would be desirable to provide an improved device and method for treating OSA.

It would also be desirable to provide treatment for various other respiratory and related disorders.

SUMMARY OF THE INVENTION

The present invention provides a novel approach to treating obstructive sleep apnea and other respiratory related disorders or conditions.

In accordance with one aspect of the invention, in a patient diagnosed with obstructive sleep apnea, tissue associated with the diaphragm or phrenic nerve is electrically stimulated to prevent obstructive respiratory events.

In accordance with one aspect of the invention stimulation of the diaphragm or phrenic nerve is provided to such obstructive sleep apnea patients to reduce the occurrence of upper airway collapse or upper airway flow limitation.

In accordance with one aspect of the invention, a device and method for increasing functional residual capacity (i.e., end expiratory lung volume) is provided.

In accordance with one aspect of the invention, a device and method for increasing upper airway patency is provided.

In accordance with one aspect of the invention, a device and method are provided for providing ventilatory stability in an obstructive sleep apnea patient.

In accordance with one aspect of the invention, an indicator of an impending obstructive respiratory event is detected prior to event onset.

In accordance with one aspect of the invention, a method for mitigating (i.e., preventing or lessening) obstructive respiratory events is provided.

In accordance with one aspect of the invention, a method and device is provided for synchronizing stimulation with one or more portions of an intrinsic breathing cycle.

In accordance with one aspect of the invention, a device and method for eliciting deep inspiration while avoiding airway closure are provided.

In accordance with one aspect of the invention, a device and method for normalizing peak flow while increasing tidal volume are provided.

In accordance with one aspect of the invention, a device and method for manipulating exhalation are provided.

In accordance with one aspect of the invention, a device and method for entraining breathing are provided.

In accordance with another aspect of the invention, a device detects when an obstruction has occurred to a particular extent and refrains from stimulating if the collapse has occurred to a particular extent.

In accordance with another aspect of the invention, a low level of stimulation is provided for therapeutic effects.

In accordance with another aspect of the invention, a low level of stimulation to the diaphragm or phrenic nerve is provided through or after airway closure to speed up airway opening and reduce arousal.

These and other inventions are described herein and/or set forth in the claims herein.

BRIEF DESCRIPTION OF THE DRAWINGS

FIGS. 11A and 11B are schematic illustrations respectively of respiration response and stimulation waveforms illustrating a stimulation method using a stimulation device according to the invention.

FIGS. 12A, 12B and 12C are schematic illustrations respectively of flow and tidal volume respiration response and stimulation waveforms illustrating a stimulation method using a stimulation device according to the invention.

FIGS. 14A and 14B are schematic illustrations respectively of respiration response and stimulation waveforms illustrating a stimulation method using a stimulation device according to the invention.

FIG. 16B is a schematic example of a waveform of an integrated signal processed by the signal processor of FIG. 16A.

FIG. 16C is a schematic EMG envelope waveform.

FIG. 16D is a schematic waveform corresponding to or correlated with air flow.

DETAILED DESCRIPTION

In accordance with one aspect of the invention, a method and device for treating obstructive sleep apnea patients is provided. According to one embodiment, a device is provided that manipulates breathing according to one or more protocols, by stimulating the diaphragm or phrenic nerve to mitigate or prevent obstructive respiratory events including obstructive sleep apnea or other events with an obstructive component. The device may comprise a phrenic nerve or diaphragm stimulator and a sensor configured to sense a condition of a subject indicating a possibility that an obstructive respiratory event will occur or is occurring. In accordance with the invention, obstructive respiratory events are characterized by a narrowing of the air passageway, typically the upper air passageway. Examples of obstructive respiratory events include but are not limited to obstructive sleep apnea, obstructive hypopnea and other respiratory events with an obstructive component.

In another embodiment, stimulation is applied at a low level through or after an obstructive respiratory event has occurred.

In addition, in accordance with the invention stimulation techniques for controlling or manipulating breathing may be used for therapeutic purposes in other non-OSA patients.

Figure 1:
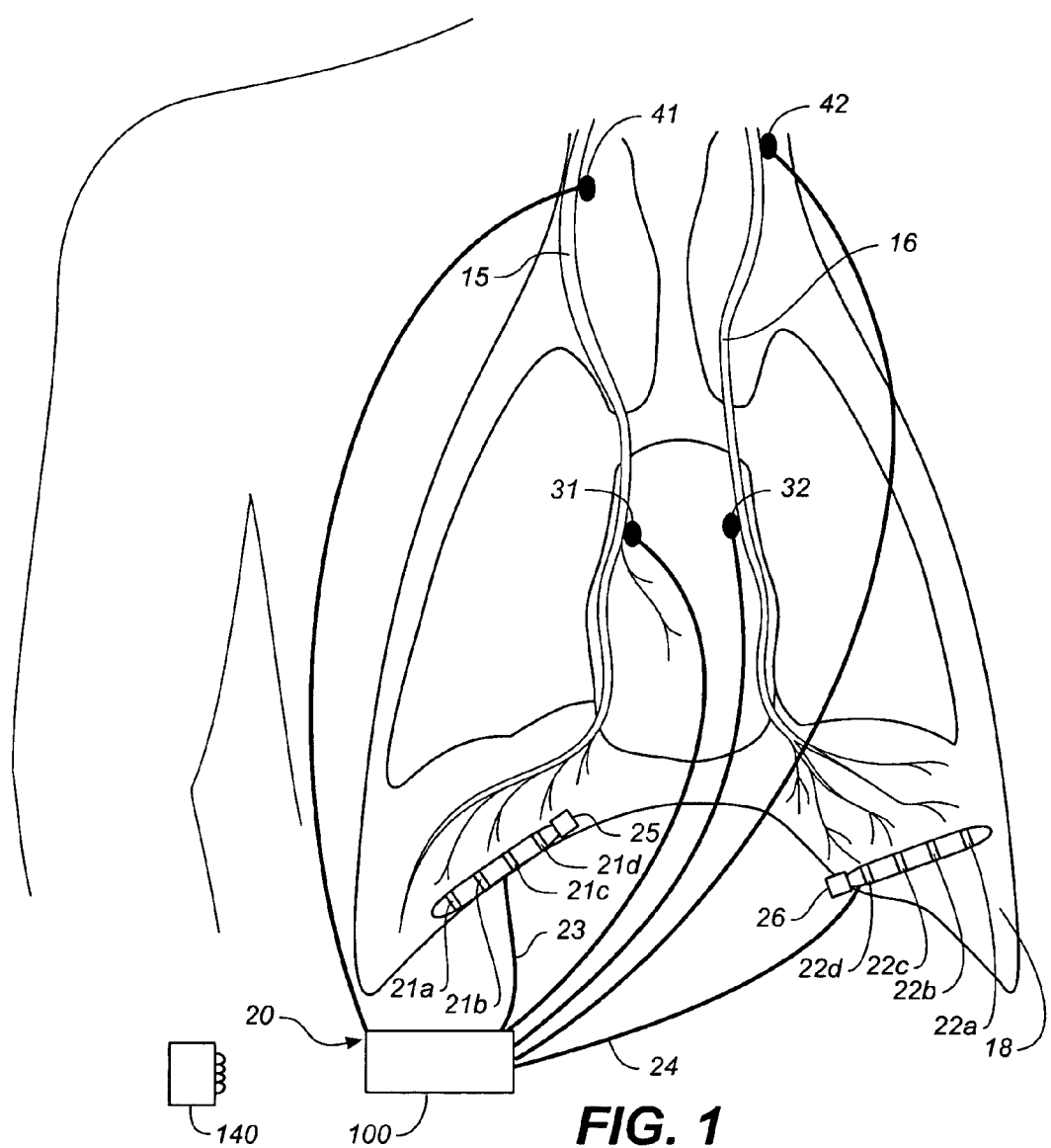
FIG. 1 is a schematic illustration of a device implanted in a subject in accordance with the invention.
Figure 2:
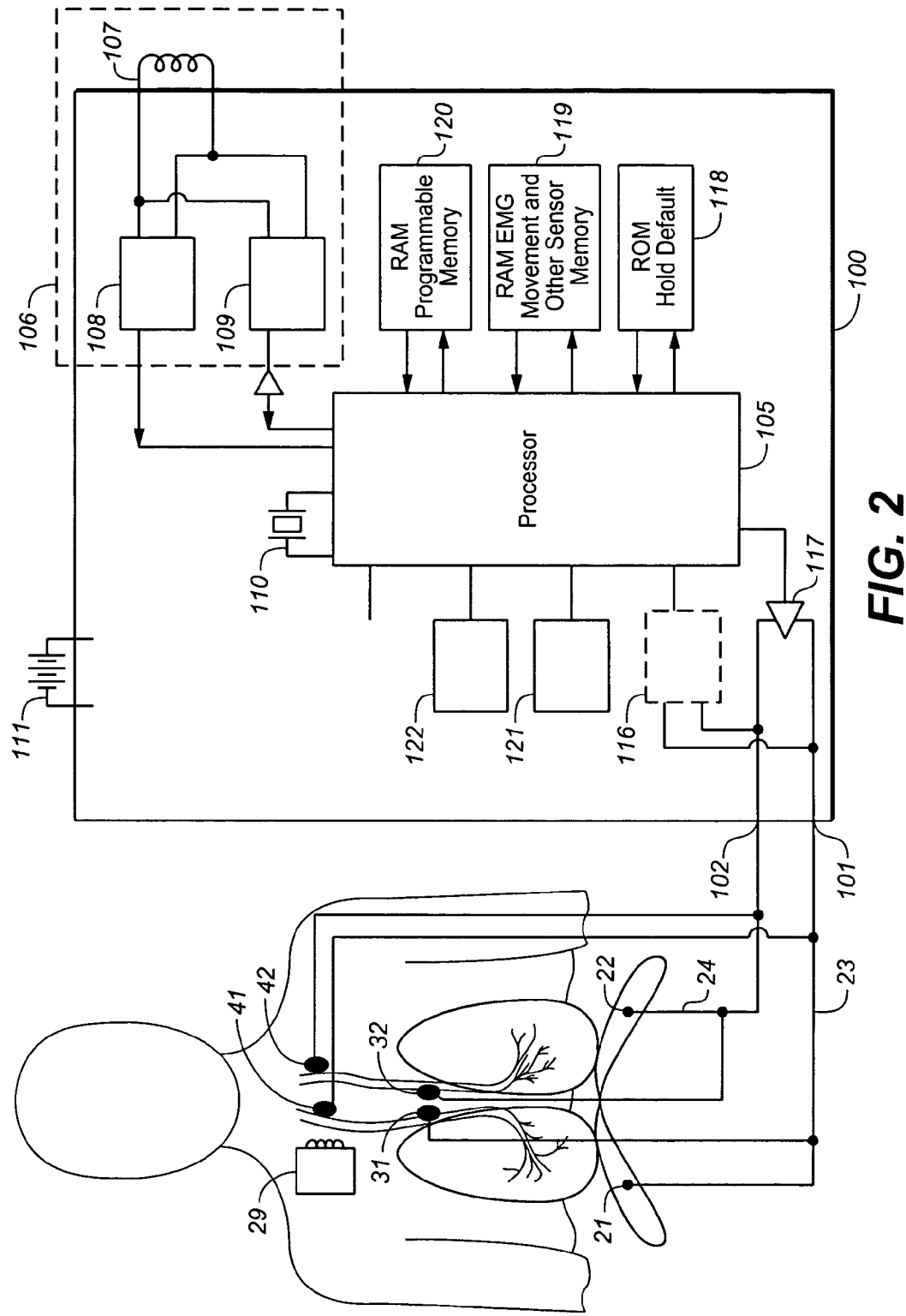
FIG. 2 is a schematic illustration of a processor unit of a sleep breathing disorder treatment device in accordance with the invention.

FIGS. 1 and 2 illustrate a stimulator 20 comprising electrode assemblies 21, 22, each comprising a plurality of electrodes 21a-d and 22a-d respectively. The electrode assemblies 21, 22 are implanted in the diaphragm muscle so that one or more of electrodes 21a-d and of electrodes 22a-d are approximately adjacent to one or more of the junctions of the phrenic nerves 15, 16, respectively, with the diaphragm 18 muscle. Alternatively or additionally, electrodes or electrode assemblies may be implanted on the diaphragm from the thoracic side, at a location along the phrenic nerve in the thoracic region, neck region or other location adjacent a phrenic nerve (e.g. transvenously) where stimulating the phrenic nerve affects breathing and/or diaphragm movement of the subject. In addition, leads may be subcutaneously placed to stimulate at least a portion of the diaphragm or phrenic nerve. The electrode assemblies 21, 22, 31, 32, 41, 42 described herein are coupled to outputs of a pulse generator and are configured to deliver electrically stimulating signals to tissue associated with the implanted electrode assemblies.

The electrode assemblies 21, 22 (31, 32, 41, 42) may sense as well as pace or electrically stimulate at the diaphragm muscle or at the phrenic nerve. Electrode assemblies 21, 22 may be implanted laparoscopically through the abdomen and into the muscle of the diaphragm 18 with needles, tissue expanding tubes, cannulas or other similar devices. The electrode assemblies 21, 22 may be anchored with sutures, staples, or other anchoring mechanisms. The electrode assemblies 21, 22 may be surface electrodes or alternatively intramuscular electrodes. The leads 23, 24 coupling the electrode assemblies 21, 22 to the control unit 100 are routed subcutaneously to the side of the abdomen where a subcutaneous pocket is created for the control unit 100. The electrode assemblies 21, 22 are each flexible members with electrodes 21a-d, assembled about 1-20 mm apart from one another and electrodes 22a-d assembled about 1-20 mm apart from one another. The electrode assemblies 21, 22 are coupled via leads 23, 24 to control unit 100. The stimulator 20 further comprises one or more sensors configured to sense one or more physiologic parameters. For example one or more sensors such as an accelerometer or movement sensor may sense information regarding movement pattern of the diaphragm muscles, intercostal muscles, and rib movement and thus determine overall respiratory activity and patterns. An electrode or electrodes may be used to sense the EMG of the diaphragm to determine respiration parameters. A flow sensor may be implanted in or near the trachea to sense tracheal air flow. These sensors may be incorporated with electrode leads 21, 22, 31, 32, 41, 42 or may be separately implanted or otherwise coupled to the subject.

The control unit 100 is configured to receive and process signals corresponding to sensed physiological parameters, e.g., flow, nerve activity, diaphragm or intercostal muscle movement, and/or EMG of the diaphragm 18, to determine the respiratory parameters of the diaphragm 18. An EMG signal may be used or other sensed activity may also correspond with either tidal volume or airflow and may be used to identify different portions of a respiration cycle. An example of such signal processing or analysis is described in more detail herein with reference to a sensed respiration correlated signal, such as an EMG, flow or tidal volume correlated signal, in FIGS. 16A-16D.

The electrodes assemblies 21, 22 are coupled via leads 23, 24 to input/output terminals 101, 102 of a control unit 100. The leads 23, 24 comprise a plurality of electrical connectors and corresponding lead wires, each coupled individually to one of the electrodes 21a-d, 22a-d. Alternatively or in addition, electrodes 31, 32 implanted on or near the phrenic nerve in the thoracic region or electrodes 41, 42 implanted on or near the phrenic nerve in the neck region. Other locations at or near the phrenic nerve may be stimulated as well. Electrodes may be placed at or near the hypoglossal nerve in accordance with a variation of the invention where stimulation of the diaphragm is coordinated with activation of upper airway muscles to open the airway passage just prior to stimulating the diaphragm muscles.

The control unit 100 is implanted subcutaneously within the patient, for example in the chest region on top of the pectoral muscle. The control unit may be implanted in other locations within the body as well. The control unit 100 is configured to receive sensed nerve electrical activity from the electrode assemblies 21, 22, (31, 32, 41, 42) corresponding to respiratory effort or other respiration related parameters of a patient. The control unit 100 is also configured to receive information corresponding to other physiological parameters as sensed by other sensors. The control unit 100 delivers stimulation to the nerves 15, 16 or diaphragm as desired in accordance with the invention. The control unit 100 may determine when to stimulate as well as specific stimulation parameters based on sensed information.

Additional sensors may comprise movement detectors 25, 26, in this example, strain gauges or piezo-electric sensors included with the electrode assemblies 21, 22 respectively and electrically connected through leads 23, 24 to the control unit 100. The movement detectors 25, 26 detect movement of the diaphragm 18 and thus the respiration parameters. The movement detectors 25, 26 sense mechanical movement and deliver a corresponding electrical signal to the control unit 100 where the information is processed by the processor 105. The movement information correlates to airflow and may accordingly be used to determine related respiration parameters.

Electrodes may be selected from the plurality of electrodes 21a-d and 22a-d once implanted, to optimize the stimulation response. Electrodes may also be selected to form bipolar pairs or multipolar groups to optimize stimulation response. Alternatively electrodes may be in a monopolar configuration. Testing the response may be done by selecting at least one electrode from the electrodes in an assembly or any other combination of electrodes to form at least one closed loop system, by selecting sequence of firing of electrode groups and by selecting stimulation parameters. The electrodes may be selected by an algorithm programmed into the processor that determines the best location and sequence for stimulation and/or sensing nerve and/or EMG signals, e.g., by testing the response of the electrodes by sensing respiratory effort or flow in response to stimulation pulses. Alternatively, the selection process may occur using an external programmer that telemetrically communicates with the processor and instructs the processor to cause stimulation pulses to be delivered and the responses to be measured. From the measured responses, the external programmer may determine the optimal electrode configuration, by selecting the electrodes to have an optimal response to delivery of stimulation.

Alternative mapping techniques may be used to place one or more stimulation electrodes on the diaphragm. Examples of mapping the diaphragm and/or selecting desired locations or parameters for desired stimulation responses are described for example in U.S. application Ser. No. 10/966,484 filed Oct. 15, 2004 and entitled: SYSTEM AND METHOD FOR MAPPING DIAPHRAGM ELECTRODE SITES; in U.S. application Ser. No. 10/966,474, filed Oct. 15, 2004 entitled: BREATHING THERAPY DEVICE AND METHOD; in U.S. application Ser. No. 10/966,472 filed Oct. 15, 2004 entitled: SYSTEM AND METHOD FOR DIAPHRAGM STIMULATION; U.S. application Ser. No. 10/966,421 filed Oct. 15, 2004 entitled: BREATHING DISORDER AND PRECURSOR PREDICTOR AND THERAPY DELIVERY DEVICE AND METHOD; and in U.S. application Ser. No. 10/686,891 filed Oct. 15, 2003 entitled BREATHING DISORDER DETECTION AND THERAPY DELIVERY DEVICE AND METHOD, all of which are fully incorporated herein by reference.

FIG. 2 illustrates an implantable control unit 100. The control unit 100 includes electronic circuitry capable of generating and/or delivering electrical stimulation pulses to the electrodes or electrode assemblies 21, 22, 31, 32, 41, 42, through leads 23, 24, 33, 34, 43, 44, respectively, to cause a diaphragm respiratory response in the patient. For purposes of illustration, in FIG. 2, the control unit 100 is shown coupled through leads 23, 24 to electrode assemblies 21, 22 respectively. Other leads as described herein may be connected to inputs 101, 102.

The control unit 100 comprises a processor 105 for controlling the operations of the control unit 100. The processor 105 and other electrical components of the control unit are coordinated by an internal clock 110 and a power source 111 such as, for example a battery source or an inductive coupling component configured to receive power from an inductively coupled external power source. The processor 105 is coupled to a telemetry circuit 106 that includes a telemetry coil 107, a receiver circuit 108 for receiving and processing a telemetry signal that is converted to a digital signal and communicated to the processor 105, and a transmitter circuit 109 for processing and delivering a signal from the processor 105 to the telemetry coil 107. The telemetry coil 107 is an RF coil or alternatively may be a magnetic coil. The telemetry circuit 106 is configured to receive externally transmitted signals, e.g., containing programming or other instructions or information, programmed stimulation rates and pulse widths, electrode configurations, and other device performance details. The telemetry circuit is also configured to transmit telemetry signals that may contain, e.g., modulated sensed and/or accumulated data such as sensed EMG activity, sensed flow or tidal volume correlated activity, sensed nerve activity, sensed responses to stimulation, sensed position information, sensed movement information and episode counts or recordings.

The leads 23, 24 are coupled to inputs 101, 102 respectively, of the control unit 100, with each lead 23, 24 comprising a plurality of electrical conductors each corresponding to one of the electrodes or sensors (e.g., movement sensor) of the electrode assemblies 23, 24. Thus the inputs 101, 102 comprise a plurality of inputs, each input corresponding to one of the electrodes or sensors. The signals sensed by the electrode assemblies 21, 22 are input into the control unit 100 through the inputs 101, 102. Each of the inputs are coupled to a separate input of a signal processing circuit 116 (schematically illustrated in FIG. 2 as one input) where the signals are then amplified, filtered, and further processed, and where processed data is converted into a digital signal and input into the processor 105. Each signal from each input is separately processed in the signal processing circuit 116.

The EMG/Phrenic nerve sensing has a dual channel sensor. One corresponding to each lung/diaphragm side. However, sensing can be accomplished using a single channel as the brain sends signals to the right and left diaphragm simultaneously. Alternatively, the EMG or phrenic nerve collective may be sensed using a single channel. Either a dual channel or single channel setting may be used and programmed.

The control unit 100 further includes a ROM memory 118 coupled to the processor 105 by way of a data bus. The ROM memory 118 provides program instructions to the control unit 100 that direct the operation of the stimulator 20. The control unit 100 further comprises a first RAM memory 119 coupled via a data bus to the processor 105. The first RAM memory 119 may be programmed to provide certain stimulation parameters such as pulse or burst morphology; frequency, pulse width, pulse amplitude, duration and a threshold or trigger to determine when to stimulate. A second RAM memory 120 (event memory) is provided to store sensed data sensed, e.g., by the electrodes of one or more electrode assemblies 21, 22 (EMG or nerve activity), position sensor 121, diaphragm movement sensors or strain gauges 25, 26, or the accelerometer 122 or other sensors such as a flow or tidal volume correlated sensors (e.g. using movement sensors or impedance plethysmography with a sensor positioned at one or more locations in the body such as on the control unit 100. These signals may be processed and used by the control unit 100 as programmed to determine if and when to stimulate or provide other feedback to the patient or clinician. Also stored in RAM memory 120 may be the sensed waveforms for a given interval, and a count of the number of events or episodes over a given time as counted by the processor 105. The system's memory will be programmable to store information corresponding to breathing parameters or events, stimulation delivered and responses, patient compliance, treatment or other related information. These signals and information may also be compiled in the memory and downloaded telemetrically to an external device 140 when prompted by the external device 140.

Figure 16A:
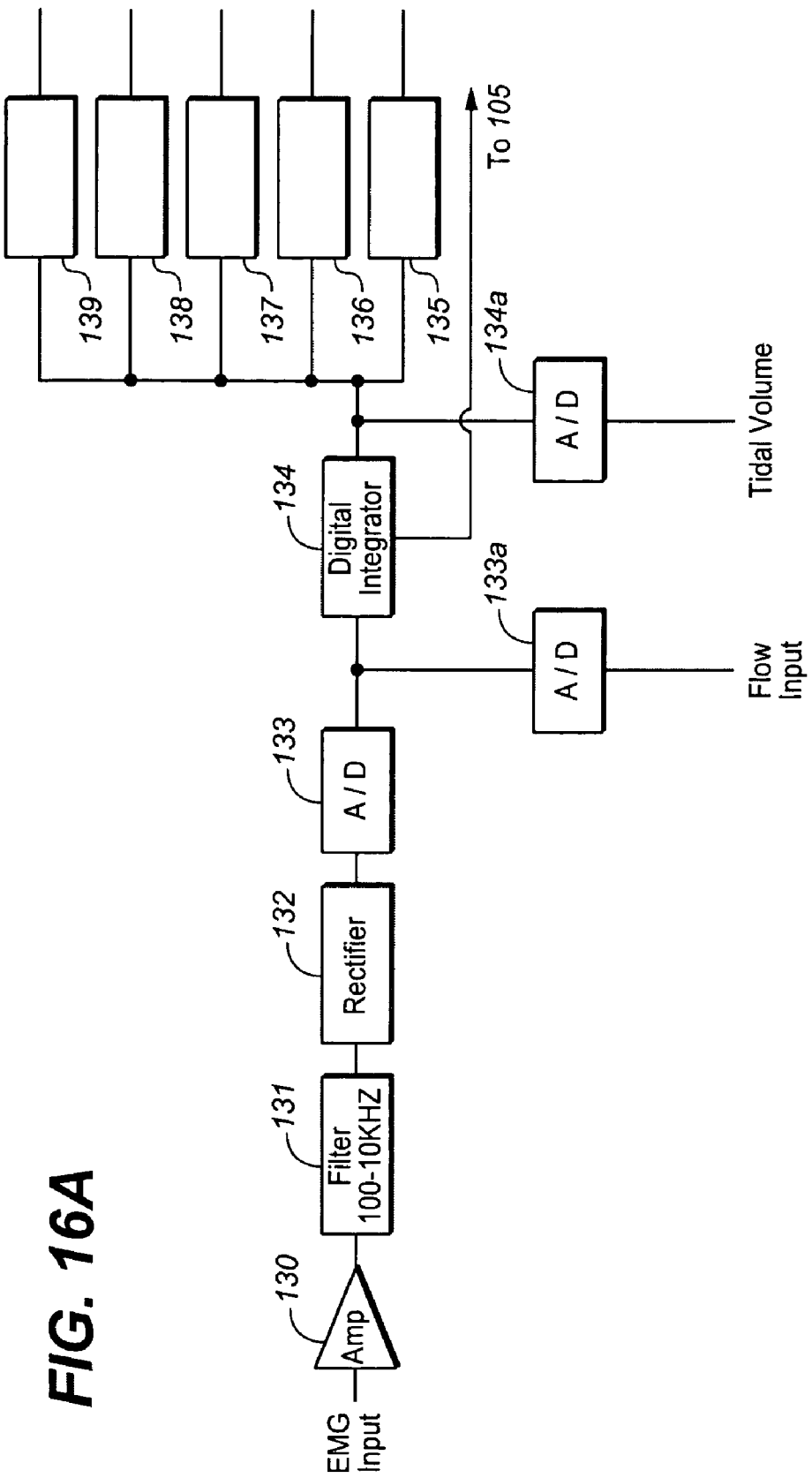
FIG. 16A is a schematic of a signal processor of the processor unit in accordance with the invention.

An example of the circuits of the signal processing circuit 116 corresponding to one or more of the sensor inputs is illustrated schematically in FIG. 16A. A sensor input signal correlating or corresponding to EMG, tidal volume or flow is input into an amplifier 130 that amplifies the signal. The signal is then filtered to remove noise by filter 131. The amplified signal is rectified by a rectifier 132, is converted by an A/D converter 133 and then is integrated by integrator 134 to result in an integrated signal from which respiratory information can be ascertained. A flow correlated signal may be input through A/D converter 133*a* and then input through the integrator 134. The signal output of the integrator 134 is then coupled to the processor 105 and provides a digital signal corresponding to the integrated waveform to the processor 105. A tidal volume correlated signal may also be input to the signal processing circuit through A/D converter 134*a* at the output of the integrator 134. The signal output of the integrator 134 is coupled to a peak detector 135 that determines when the inspiration period of a respiratory cycle has ended and an expiration cycle has begun. The signal output of the integrator 134 is further coupled to a plurality of comparators 136, 137. The first comparator 136 determines when respiration has been detected based on when an integrated signal waveform amplitude has been detected that is greater than a percentage value of the peak of an intrinsic respiratory cycle or another predetermined amount (comp 1), for example between 1-25% of the intrinsic signal. In this example, the comparator is set at a value that is 10% of the waveform of an intrinsic respiratory cycle. The second comparator 137 determines a value of the waveform amplitude (comp 2) when an integrated signal waveform amplitude has been detected that is at a predetermined percentage value of the peak of an intrinsic respiratory cycle or another predetermined amount, for example between 75%-100% of the intrinsic signal. In this example, the comparator is set at a value that is 90% of the waveform of an intrinsic respiratory cycle. From this value and the comp 1 value, the slope of the inspiration period (between 10% and 90% in this example) may be determined. This slope may provide valuable diagnostic information as it shows how quickly a patient inhales.

In the case of a signal correlating to flow that is integrated or a signal correlated to tidal volume, after (or when) the peak detector detects the end of an inhalation period and the beginning of an exhalation period, the third comparator 138 determines an upper value for the waveform amplitude during active exhalation period, for example between 100% and 75% of the peak value detected by the peak detector 135. Then a lower value (comp 4) of the waveform during the exhalation period is determined by the fourth comparator 139, which compares the measured amplitude to a predetermined value, e.g. a percentage value of the peak amplitude. In this example, the value is selected to be 10% of the peak value. In one embodiment this value is selected to roughly coincide with the end of a fast exhalation period. From comp 3 and comp 4 values, the slope of the exhalation period (between 10% and 90% in this example) may be determined. This slope may provide valuable diagnostic information as it shows how quickly a patient exhales.

A non-integrated flow signal may also be used, for example in conjunction with EMG to detect airway closure where EMG is present in the absence of flow.

FIG. 16B illustrates two sequential integrated waveforms of exemplary integrated signals corresponding to two serial respiratory cycles. An inspiration portion 172 may be observed using an EMG, flow or tidal volume correlated signal. An exhalation period 176 may be observed using a flow or tidal volume correlated signal. The waveform 170 has a baseline 170*b*, inspiration cycle 171, a measured inspiration cycle 172, a point of 10% of peak inspiration 173 (comp 1), a point of 90% of peak of inspiration 174 (comp 2), a peak 175 where inspiration ends and exhalation begins, and exhalation cycle 176 a fast exhalation portion 177 of the exhalation cycle 176, a 90% of peak exhalation point 178 (comp 3), a 10% of peak exhalation point 179 (comp 4), an actual respiratory cycle 180 and a measured respiratory cycle 181. The second waveform 182 is similarly shaped. The 10% inspiration 183 of the second waveform 182 marks the end of the measured respiratory cycle 181, while the 10% point 173 of the waveform 170 marks the beginning of the measured respiratory cycle 181.

FIG. 16C illustrates a schematic EMG envelope corresponding to an inspiration portion e.g., 172 of a respiration cycle. FIG. 16D illustrates a schematic flow correlated signal corresponding to a respiration cycle.

Figure 3:
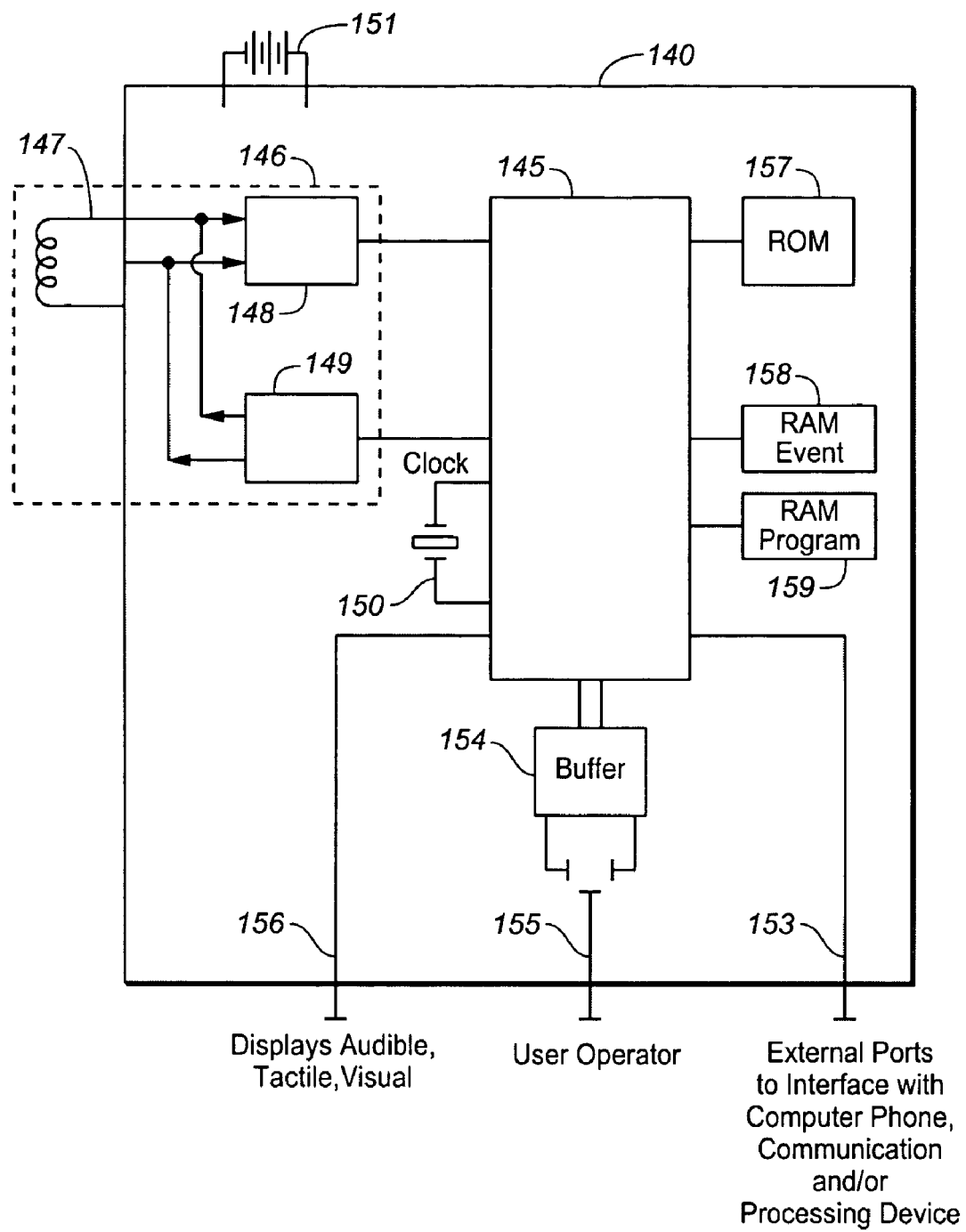
FIG. 3 is a schematic illustration of an external device of a stimulator in accordance with the invention.

In FIG. 3 a circuit for an external device 140 is illustrated. The external device 140 comprises a processor 145 for controlling the operations of the external device. The processor 145 and other electrical components of the external device 140 are coordinated by an internal clock 150 and a power source 151. The processor 145 is coupled to a telemetry circuit 146 that includes a telemetry coil 147, a receiver circuit 148 for receiving and processing a telemetry signal that is converted to a digital signal and communicated to the processor 145, and a transmitter circuit 149 for processing and delivering a signal from the processor 145 to the telemetry coil 146. The telemetry coil 147 is an RF coil or alternatively may be a magnetic coil depending on what type of coil the telemetry coil 107 of the implanted control unit 100 is. The telemetry circuit 146 is configured to transmit signals to the implanted control unit 100 containing, e.g., programming or other instructions or information, programmed stimulation protocols, rates and pulse widths, electrode configurations, and other device performance details. The telemetry circuit 146 is also configured to receive telemetry signals from the control unit 100 that may contain, e.g., sensed and/or accumulated data such as sensed information corresponding to physiological parameters, (e.g., sensed EMG activity, sensed nerve activity, sensed responses to stimulation, sensed position information, sensed flow, or sensed movement information). The sensed physiological information may be stored in RAM event memory 158 or may be uploaded and through an external port 153 to a computer, or processor, either directly or through a phone line or other communication device that may be coupled to the processor 145 through the external port 153. The external device 140 also includes ROM memory 157 for storing and providing operating instructions to the external device 140 and processor 145. The external device also includes RAM event memory 158 for storing uploaded event information such as sensed information and data from the control unit, and RAM program memory 159 for system operations and future upgrades. The external device also includes a buffer 154 coupled to or that can be coupled through a port to a user-operated device 155 such as a keypad input or other operation devices. Finally, the external device 140 includes a display device 156 (or a port where such device can be connected), e.g., for display visual, audible or tactile information, alarms or pages.

The external device 140 may take or operate in, one of several forms, e.g. for patient use, compliance or monitoring; and for health care provider use, monitoring, diagnostic or treatment modification purposes. The information may be downloaded and analyzed by a patient home unit device such as a wearable unit like a pager, wristwatch or palm sized computer. The downloaded information may present lifestyle modification, or compliance feedback. It may also alert the patient when the health care provider should be contacted, for example if there is malfunctioning of the device or worsening of the patient's condition.

Other devices and methods for communicating information and/or powering stimulation electrodes as are know in the art may be used as well, for example a transcutaneously inductively coupled device may be used to power an implanted device.

According to one aspect of the invention, the stimulator operates to stimulate and/or manipulate breathing to mitigate (i.e., avoid or reduce effects of) an obstructive respiratory event by stimulating the phrenic nerve, diaphragm or associated tissue according to one or more protocols, to elicit a respiratory response. Examples of such stimulation protocols are described herein with reference to FIGS. 4A-16D. In accordance with another aspect of the invention, such stimulation is provided prior to the onset of an obstructive respiratory event or prior to airway obstruction to prevent an obstructive respiratory event from occurring or the airway from fully closing. In accordance with another aspect of the invention, stimulation is provided at a low level following obstructive sleep apnea or effective airway closure.

In accordance with one aspect of the invention as described with respect to FIGS. 4A-4D, 5A-5C, 7A-7B, 8A-8B, 9A-9C, 10A-10C and 12A-12B, stimulation of the phrenic nerve or diaphragm is provided to increase functional residual capacity, i.e., end expiratory volume, at least until onset of a subsequent respiration cycle. In accordance with the invention, an increased functional residual capacity is believed to assist in maintaining an airway passage open to a sufficient degree to prevent or reduce airway collapse that results in an obstructive respiratory event.

In accordance with another aspect of the invention, as described with respect to FIGS. 4A-4D, 5A-5B, 6A-6B, 10A-10C, 11A-11B, 12A-12B or 14A-14B, stimulation of the phrenic nerve or diaphragm is provided to increase tidal volume sufficiently to increase upper airway patency. It is believed that increasing the tidal volume may contribute to stiffening the upper airway. Preferably the same or a lower peak flow with respect to intrinsic flow is provided to avoid an increase in negative pressure applied to the upper airway that would decrease upper airway patency. Therapy may be delivered to increase flow in the case where flow is below normal. In cases where flow is normal, or limited by obstruction, tidal volume may be increased through extension of the inspiration duration. An upper airway hysteresis effect may also occur where the volume of a breath is increased above a normal tidal volume and the stiffening of the upper airway during inspiration does not return entirely to a relaxed resting state. It is accordingly additionally believed that an upper airway hysteresis effect would stiffen the upper air passageway for subsequent breaths and will thereby prevent or mitigate airway narrowing or collapse that results in obstructive sleep apnea.

In accordance with one aspect of the invention, as described with respect to FIGS. 9A-9C, 11A-11B, 13A-13B and 14A-14B, stimulation is provided to create ventilatory stability and to thereby reduce fluctuations in the upper airway passage muscles that may lead to upper airway collapse where ventilatory drive is low or unstable. "Ventilatory instability is defined herein to mean varying breathing rate and/or tidal volume outside of normal variations." Ventilatory stability associated with obstructive respiratory events, as opposed to periodic breathing or Cheynes-Stokes respiration, include, for example, variations in breathing rate and/or tidal volume associated with sleep onset, change in sleep state, and REM sleep.

In accordance with another aspect of the invention, as described with respect to FIGS. 4A-4D, 6A-6C, 9A-9C and 10A-10C, 11A-11B, 12A-12B, and 14A-14B, stimulation of the phrenic nerve or diaphragm is provided during intrinsic breathing during or at the end of an intrinsic inspiration portion of a breathing cycle. For purposes of the invention herein, the intrinsic cycle may be detected near onset of inspiration. Other portions of a breathing cycle may be identified for breathing stimulation. Alternatively, the beginning of the breathing cycle or a portion of the breathing cycle may be predicted, e.g., based on a typical breathing pattern of an individual patient.

A stimulation signal may be provided during inspiration of intrinsic breathing for various purposes. In accordance with a variation of the invention, stimulation is provided during intrinsic inspiration to provide initial and more gradual control of breathing according to a protocol. Then, breathing control protocols may be applied so that airway closure due to stimulation is avoided. Tidal volume is increased gradually so as to balance out an increase in upper airway resistance that can occur with stimulation during intrinsic inspiration. Stimulation of breathing during intrinsic inspiration in accordance with variations of the invention is configured to contribute to creating the effect of increasing functional residual capacity. In some variations of the invention, stimulation during intrinsic breathing is configured to stiffen the upper airway, thereby increasing upper airway patency. Stimulating during inspiration in accordance with a protocol of the invention may also increase upper airway hysteresis. In one embodiment, breathing is stimulated at least in part during intrinsic inspiration so that the resulting tidal volume is greater than intrinsic normal volume, while peak flow is maintained near normal peak flow to avoid upper airway closure. Stimulating during intrinsic inspiration may also be used to normalize breathing in an obstructive sleep apnea patient and to increase ventilatory stability associated with airway obstructions. Stimulating at least in part during intrinsic inspiration may increase inspiration duration which may allow increase of tidal volume without significantly increasing the peak flow. (Increasing peak flow may increase the possibility of airway closure.) According to one embodiment, peak flow is provided at, near or below intrinsic peak flow.

While stimulating breathing during intrinsic inspiration is described herein in use with a device and method of treating obstructive sleep apnea, other breathing or related disorders may be treated by stimulating breathing during intrinsic inspiration in accordance with another aspect of the invention.

In accordance with another aspect of the invention and as illustrated in FIGS. 4A-4D, and 5A-5C the phrenic nerve or diaphragm is stimulated to provide deep inspiration therapy to a subject. Deep inspiration therapy involves stimulating a breath that is of a greater tidal volume than a normal breath. According to a preferred embodiment, deep inspiration stimulation provides a breath having a greater inspiration duration than that of a normal breath. Rather than substantially increasing peak flow or rather than increasing the magnitude of diaphragm contraction, the increase in inspiration duration to increase tidal volume is believed to reduce the likelihood of airway closure with stimulation. Deep inspiration stimulation may be provided intermittently throughout the night or a portion of the night while a patient sleeps, thus preventing an obstructive respiratory event. While deep inspiration therapy is described herein in use with a device and method of treating obstructive sleep apnea, other breathing or related disorders may be treated by deep inspiration therapy.

In accordance with another aspect of the invention as described with respect to FIGS. 6A-6B, 7A-7B, 8A-8B, 9A-9C, 10A-10C and 12A-12B, the exhalation cycle is manipulated to provide a therapeutic effect. According to one aspect of the invention, increased functional residual capacity is provided by manipulating the exhalation phase. Manipulation of the exhalation phase may be provided using stimulation during the exhalation phase. The exhalation phase may also otherwise be manipulated in length or duration.

In accordance with another aspect of the invention as described with respect to FIGS. 7A-7B 8A-8B, 9A-9C, and 10A-10C, a low level stimulation is applied during all or a portion of the respiration cycle. Among other therapeutic effects such stimulation may increase functional residual capacity. Such low level stimulation may be directed to provide an increased tidal volume during a rest phase of a respiration cycle by sustaining a low level contraction of the diaphragm. Typically such low level stimulation would be lower than the relative threshold for eliciting breathing. This level may vary from patient to patient and may be determined on an individual basis. It may also depend on electrode type and placement. Typically the stimulation is lower than 8 mA.

In accordance with another aspect of the invention, as described with respect to FIGS. 9A-9C, 12A-12B, 13A-13B, and 14A-14B, stimulation of the phrenic nerve or diaphragm is provided to control breathing. According to one aspect of the invention, breathing is controlled either by inhibiting respiratory drive, entraining breathing or other mechanisms. Controlling breathing according to one variation comprises stimulating to control or manipulate the central respiratory drive. Controlling breathing may include taking over breathing to control one or more parameters of a stimulated breath. Entraining breathing may include stimulating at a rate greater than but close to, or equal to the intrinsic respiratory rate until the central pattern generator activates the respiration mechanisms, which includes those of the upper airway, in phase with the stimulation. As an alternative or in addition, inspiration duration may be increased with respect to the total respiration cycle or exhalation. While controlling breathing is described herein in use with a device and method of treating obstructive sleep apnea, other breathing or related disorders may be treated by controlling breathing in accordance with another aspect of the invention.

According to another aspect of the invention stimulation is used to provide ventilatory stability. Examples of providing ventilatory stability are shown in FIGS. 9A-9C, 10A-10B, 11A-11B, 13A-13B and 14A-14B. Ventilatory stability may be provided by stimulating breathing to increase a falling tidal volume towards that of a normal breath. Ventilatory stability may also be provided by controlling breathing in a manner that creates stability. Ventilatory stability may also be provided by entraining breathing. Instability in ventilatory rate that indicates the onset of obstructive sleep apnea may be treated by controlling breathing for a preset period of time as described with respect to FIGS. 9A-9B, 13A-13B or FIGS. 14A-14B. Instability in ventilatory rate may also be treated by normalizing tidal volume using stimulation as described with respect to FIGS. 10A-10B or 11A-11B.

Referring to FIGS. 4A-4D, stimulation and respiration waveforms illustrating a method using a device in accordance with one aspect of the invention are illustrated. A device and method creates increased functional residual capacity and upper airway patency by providing deep inspiration. In this particular embodiment, deep inspiration is provided by stimulating during a portion of an inspiration cycle. Stimulation may extend beyond the duration of an intrinsic breath. The stimulation is provided to increase tidal volume by extending the duration of the inspiration cycle. (While preferably maintaining peak flow at or near intrinsic peak flow, i.e. normalizing flow.) In accordance with a protocol, stimulation through one or more electrodes associated with the diaphragm or phrenic nerve is provided to cause the diaphragm to contract to cause a deep inspiration breath. Stimulation may be provided when a characteristic preceding an obstructive respiratory event is detected. For example, if erratic breathing occurs or if the tidal volume drops below a given threshold level, then stimulation is provided. The resulting breath comprises a deep inhalation breath (i.e., a greater tidal volume than a normal, intrinsic breath.) A deep inspiration breath may then be repeated periodically to prevent further drop in tidal volume by increasing the functional residual capacity and creating upper airway stiffening. The device may also be programmed to repeat the deep breath a given number of times before ceasing the stimulation.

One possible characteristic of breathing in obstructive sleep apnea patients is a decreasing tidal volume. The ultimate closure of an air passageway in an obstructive sleep apnea event thus may be preceded by a gradual decrease in ventilatory volume. Another possible characteristic of breathing in obstructive sleep apnea patients is an erratic breathing pattern. In a patient who is diagnosed with obstructive sleep apnea, respiration may be monitored using EMG or other sensors that sense respiration parameters corresponding to tidal volume or flow (for example, diaphragm movement which corresponds to airflow may be sensed; impedance plethysmography may be used; or flow itself may be sensed using a sensor implanted in the trachea.) FIGS. 16A-16D illustrate monitoring or detection of various aspects or parameters of respiration on a breath by breath basis. Tidal volume is monitored and a decrease in tidal volume characteristic (FIG. 4A) or an erratic breathing pattern (FIG. 4B) in an obstructive sleep apnea patient is detected. (Monitored tidal volume as used herein may also include a monitored tidal volume correlated signal). Estimated minute ventilation (i.e., determined by multiplying respiratory rate times volume of a breath) may also be used to determine the impending onset of an obstructive respiratory event.

For purposes of detecting a threshold volume on a breath-by-breath basis or in real time, a programmed threshold may be set. The threshold value may be determined when initializing the device as the value at or below which preventative or mitigating treatment is required or is otherwise optimal. This value may be programmed into the device. A minimum safety threshold value may also be established below which stimulation is inhibited to prevent airway closure. As such, the minimum safety threshold may be set as a value sufficiently above a tidal volume where stimulation treatment if provided would further close an air passageway.

When monitoring tidal volume, the area under the inspiration flow curve or EMG envelope of an individual breath may be monitored to determine tidal volume of a breath. The tidal volume is compared to a threshold value for a particular patient. Other parameters may be used to identify when tidal volume has dropped below a predetermined threshold, for example baseline tidal volume rate variance over a period of time may be monitored and compared to a normal variance. The normal variance may be determined on a patient-by-patient basis and programmed into the device.

Figure 4A:
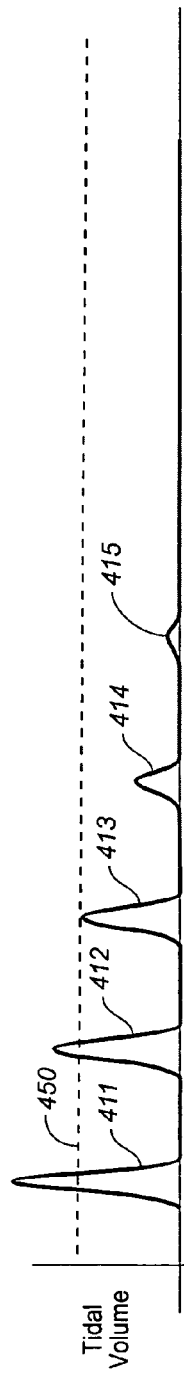
FIG. 4A is a schematic illustration of respiration of an exemplary obstructive sleep apnea patient as the patient is going into an obstructive sleep apnea event.
Figure 4B:
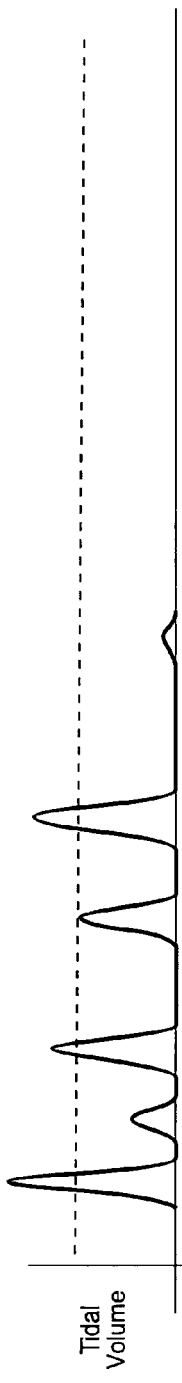
FIG. 4B is a schematic illustration of respiration of an exemplary obstructive sleep apnea patient as the patient is going into an obstructive sleep apnea event.

FIG. 4A illustrates a breathing pattern where a decrease in tidal volume ultimately ends in an obstructive sleep apnea event. Accordingly, tidal volume of intrinsic breaths 411-415 of an obstructive sleep apnea patient is shown in FIG. 4A. The tidal volume of breaths 411-415 gradually decreases until the airway narrows ultimately leading to an airway obstruction. An obstructive respiratory event occurs with total airway closure after breath 415. An obstructive respiratory event may also be an airway narrowing, e.g., hypopnea. An obstructive respiratory event may be detected by monitoring a decrease in tidal volume, for example as a predetermined percentage of normal or intrinsic tidal volume. The threshold 450 below which treatment is to be provided by the device is shown in FIGS. 4A-4D. FIG. 4D illustrates a stimulation protocol corresponding to the resulting tidal volume waveforms of FIG. 4C.

Figure 4C:
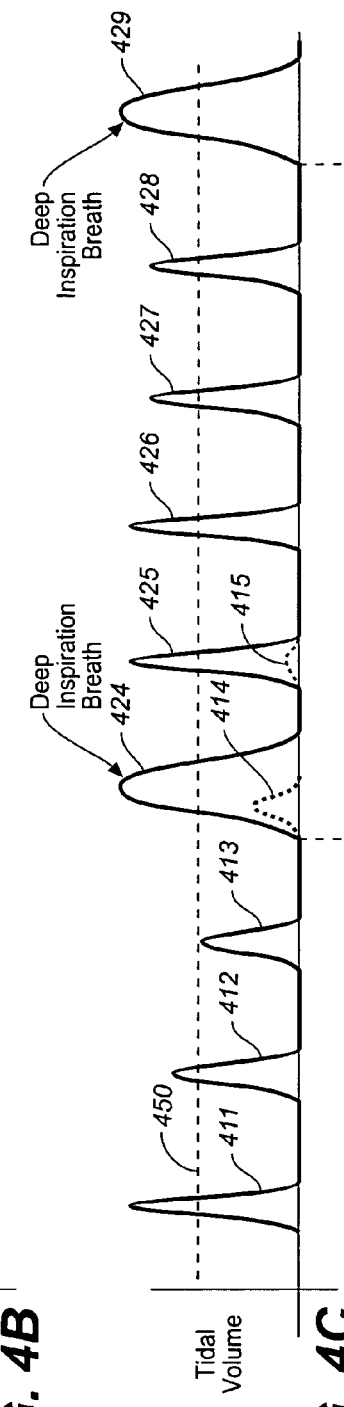
FIGS. 4C and 4D are schematic illustrations respectively of respiration response and stimulation waveforms illustrating a stimulation method using a stimulation device according to the invention in which the obstructive sleep apnea event illustrated in FIG. 4A is treated with deep inspiration stimulation.
Figure 4D:
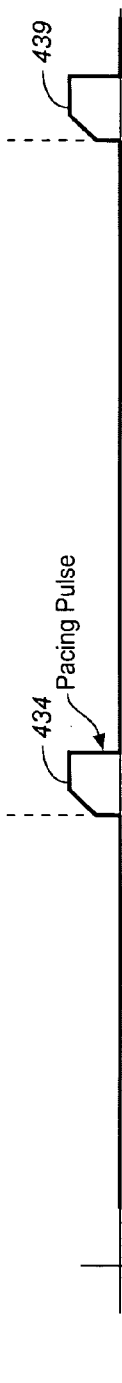

FIG. 4C illustrates tidal volume of a patient treated using a deep inspiration stimulator. The stimulator detects the drop in tidal volume (breath 413) below a threshold level as described above with respect to FIGS. 4A-4B. During the subsequent breath 414, stimulation 434 (schematically illustrated as an envelope of a burst of pulses) is provided by the stimulator to provide a deep inspiration breath 424 with the breath 414. The deep inspiration breath 424 comprises a breath that has a tidal volume greater than the tidal volume of a normal or intrinsic breath. After one or more deep inspiration breath stimulations, the tidal volume is expected to return to normal or close to normal, e.g. at breaths 425-429. Synchronization is provided whereby the onset of inspiration is detected and stimulation is provided during the breath. According to one variation, a tidal volume that is greater than or equal to a predetermined percentage of a normal inspiration is detected (e.g. 10% of tidal volume as described with respect to FIGS. 16A-16D). Then when the onset of the next inspiration is detected, stimulation is provided. Additional periodic delivery of deep inspiration paced breaths may be provided synchronously or asynchronously with the intrinsic breathing, to prevent or mitigate drops in tidal volume. In accordance with this aspect of the invention, as illustrated in FIG. 4D an additional pacing pulse or burst of pulses 439 is provided to stimulate deep inspiration breath 419. Thus, the therapy described with reference to FIG. 4D may prevent a further drop in tidal volume, thereby reducing the occurrence of obstructive respiratory events or other breathing related disorders.

Figure 5A:
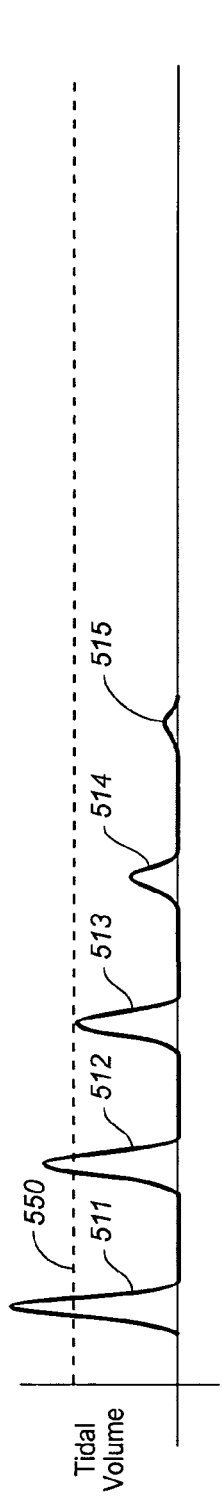
FIG. 5A is a schematic illustration of respiration of an exemplary obstructive sleep apnea patient as the patient is going into an obstructive sleep apnea event.
Figure 5B:
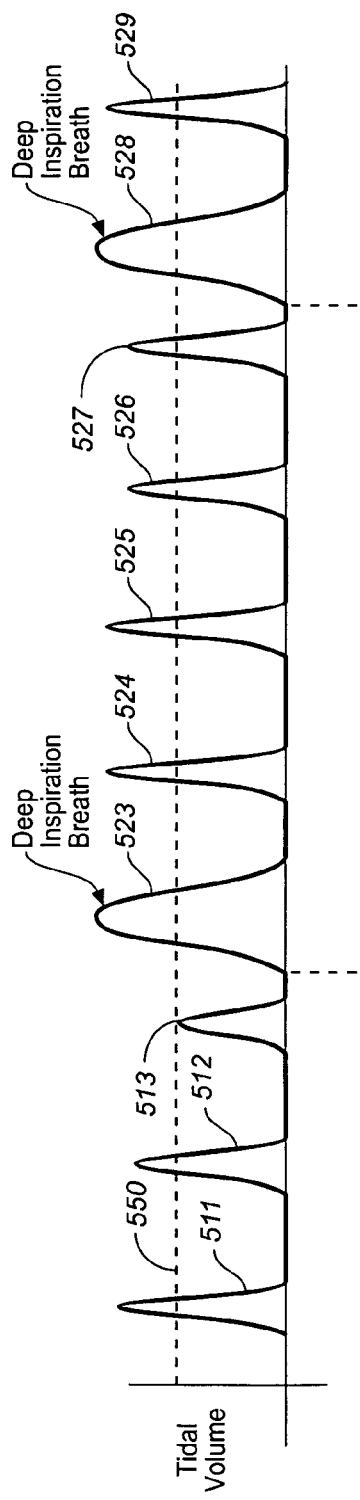
FIGS. 5B and 5C are schematic illustrations respectively of respiration response and stimulation waveforms illustrating a stimulation method using a stimulation device according to the invention in which the obstructive sleep apnea event illustrated in FIG. 5A is treated with deep inspiration stimulation.
Figure 5C:
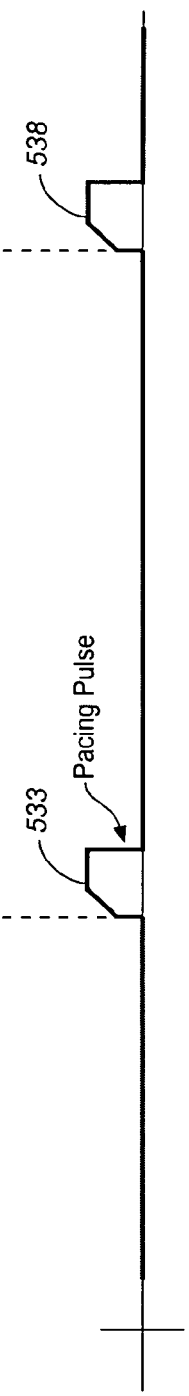

FIGS. 5A-5C illustrate use of a deep inspiration stimulator in accordance with the invention. FIG. 5A illustrates a breathing pattern where a decrease in tidal volume ultimately ends in an obstructive respiratory event. Accordingly, tidal volume of intrinsic breaths 511-515 of an obstructive sleep apnea patient is shown in FIG. 5A with the airway ultimately closing after breath 515. In FIG. 5A, no treatment is provided. Other pre-obstructive breathing characteristics may also be used to determine when an OSA event is likely to be imminent.

A threshold 550 below which treatment is to be provided by the device is shown in FIGS. 5A and 5B. This threshold may be determined in a manner similar to that described with respect to FIGS. 4A-4C. FIG. 5C illustrates a stimulation protocol corresponding to the resulting tidal volume waveforms of FIG. 5B. FIG. 5B illustrates the tidal volume of a patient treated using a deep inspiration stimulator who would otherwise have had a breathing pattern shown in FIG. 5A. The stimulator detects the drop in tidal volume (breath 513) below a threshold level 550 in a manner similar to that described above with respect to FIGS. 4A-4D. Prior to what would have been the subsequent breath 514, i.e., at some point during the intrinsic exhalation period or rest period, the stimulator provides stimulation 533 to elicit a deep inspiration breath 523 (FIG. 5B). The deep inspiration breath 523 comprises a breath with a tidal volume greater than the tidal volume of an intrinsic or normal breath. Preferably, the peak flow remains relatively normal while inspiration duration increases thus increasing tidal volume. After one or more deep inspiration breath stimulations, the tidal volume returns to normal, e.g., at breaths 524-525. At breaths 526,527 a slight decrease in respiratory drive is shown with a decreased tidal volume. Periodic delivery of deep inspiration breaths may be provided to prevent or mitigate drops in tidal volume. In accordance with this aspect of the invention, as illustrated in FIG. 5C an additional pacing pulse or burst of pulses 538 is provided prior to the onset of the next intrinsic breath to stimulate deep inspiration breath 528 which is then followed by a normal breath 529. The deep inspiration breaths 523 or 528 are intended to increase the functional residual capacity of the lung and/or enhance upper airway patency. Thus, the therapy may prevent further drop in tidal volume, thereby reducing the incidence of obstructive sleep apnea or other breathing related disorders.

Figure 6A:
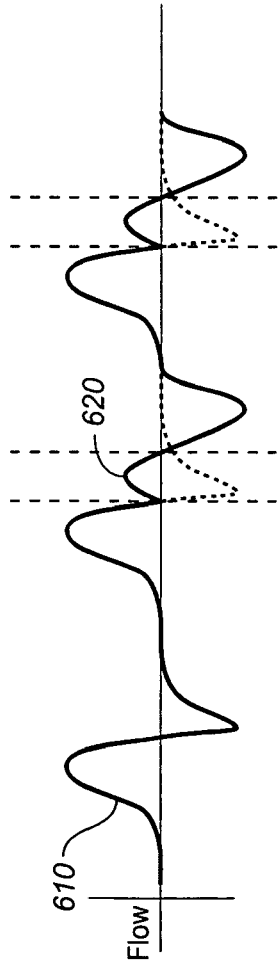
FIGS. 6A, 6B and 6C are schematic illustrations respectively of airflow, tidal volume and corresponding stimulation waveforms illustrating a stimulation method using a stimulation device according to the invention in which stimulation is applied during a portion of the respiration cycles.
Figure 6B:
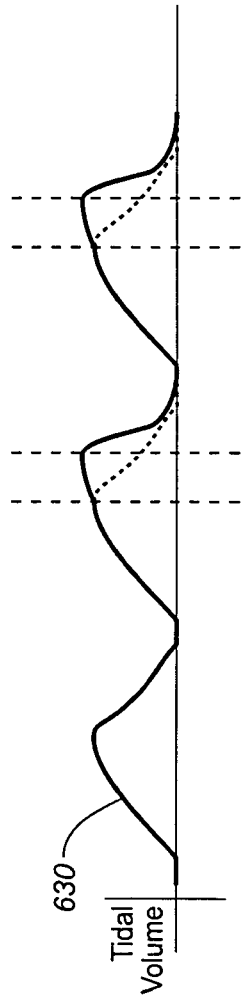
Figure 6C:
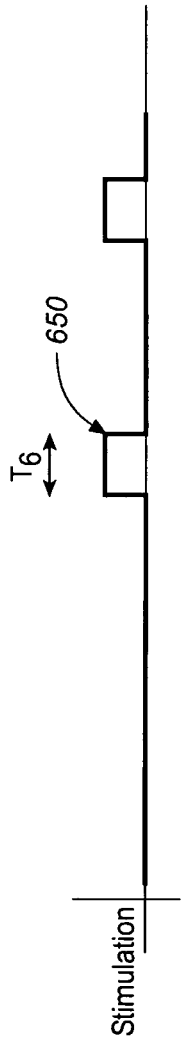

FIGS. 6A-6B illustrate stimulation and inspiration waveforms corresponding to a variation of stimulation device and method of the invention. The stimulation protocol of FIGS. 6A-6B provides stimulation at the end of an inspiration cycle increasing inspiration duration, thereby increasing tidal volume. A resulting normalized peak flow and increased tidal volume is believed to stiffen or lengthen the upper airway and may create an upper airway hysteresis effect Increased tidal volume may provide more time and volume for gas exchange. Among other effects, normalized peak flow and increased tidal volume are believed to prevent airway collapse attributable to obstructive sleep apnea.

FIG. 6A illustrates normal inspiration duration 610 of an intrinsic breath and increased inspiration duration 620 that would result from stimulation 650 shown in FIG. 6B. Stimulation 650 is provided at the end of an inspiration period for a predetermined amount of time $T_6$ to maintain flow and prolong inspiration for the additional period of time $T_6$. The end of the inspiration period may be determined in a manner as described with reference to FIGS. 16A-16D herein. The time $T_6$ may be selected and/or programmed into the device. The time may be determined to elicit a desired response. A short stimulation period, for example, as short as 0.1 seconds may be used.

Figures 7A, 7B:
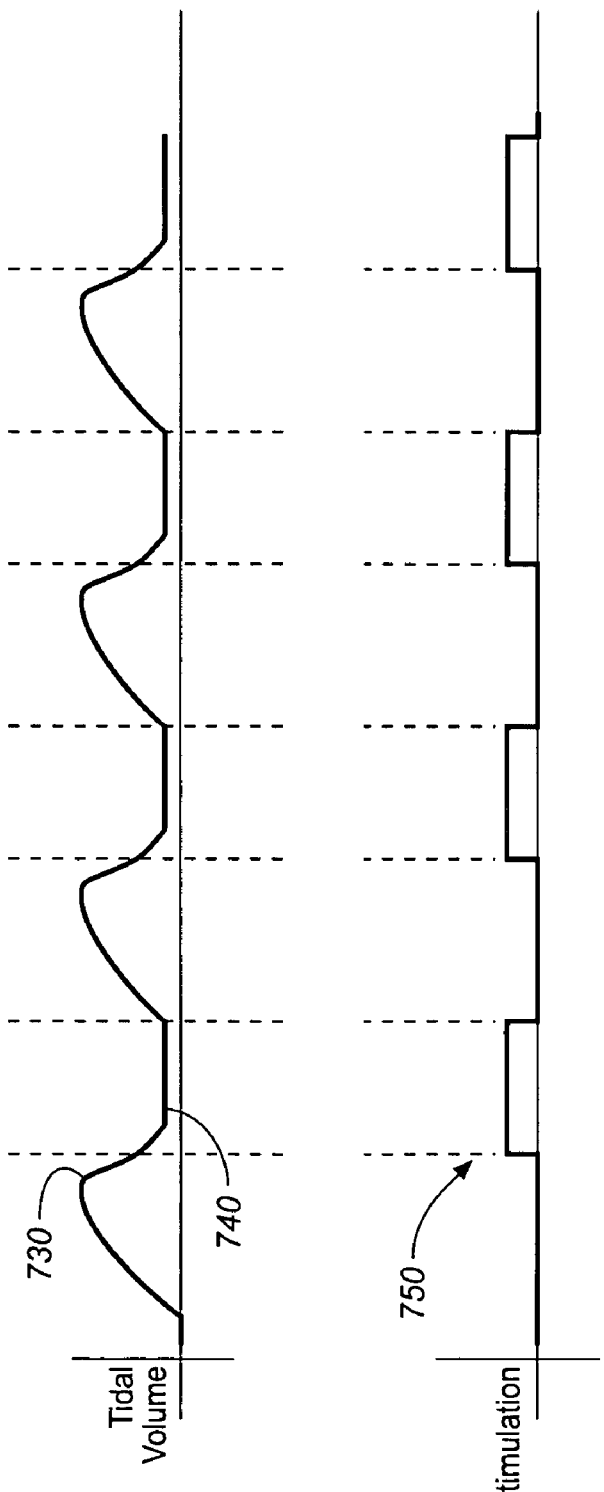
FIGS. 7A and 7B are schematic illustrations respectively of tidal volume and corresponding stimulation waveforms illustrating a stimulation method using a stimulation device according to the invention in which stimulation is applied during a portion of the respiration cycles.

FIGS. 7A-7B illustrate stimulation and inspiration waveforms corresponding to a variation of a stimulation device and method of the invention. The stimulation protocol of FIGS. 7A-7B provides low level stimulation at the beginning or the end of an exhalation portion of a respiration cycle, or at some time within the exhalation portion of the respiration cycle. This is believed to preserve lung volume prior to the next inspiration. The manipulation of the exhalation cycle is thus believed to increase functional residual capacity. FIG. 7A illustrates tidal volume 730 that would result from stimulation 750 shown in FIG. 7B. Stimulation 750 is provided at an end portion of an exhalation cycle to preserve some volume 740 for the next inspiration cycle thus increasing the functional residual capacity. The end of the exhalation cycle may be determined by determining the end of inspiration and then based on a known respiration rate, estimating the time of the end of the exhalation cycle. Alternatively, flow correlated respiration parameters may be sensed and the desired portion of the exhalation cycle may be determined. FIGS. 16A-16D illustrate manners for determining portions of a respiration cycle.

Figures 8A, 8B:
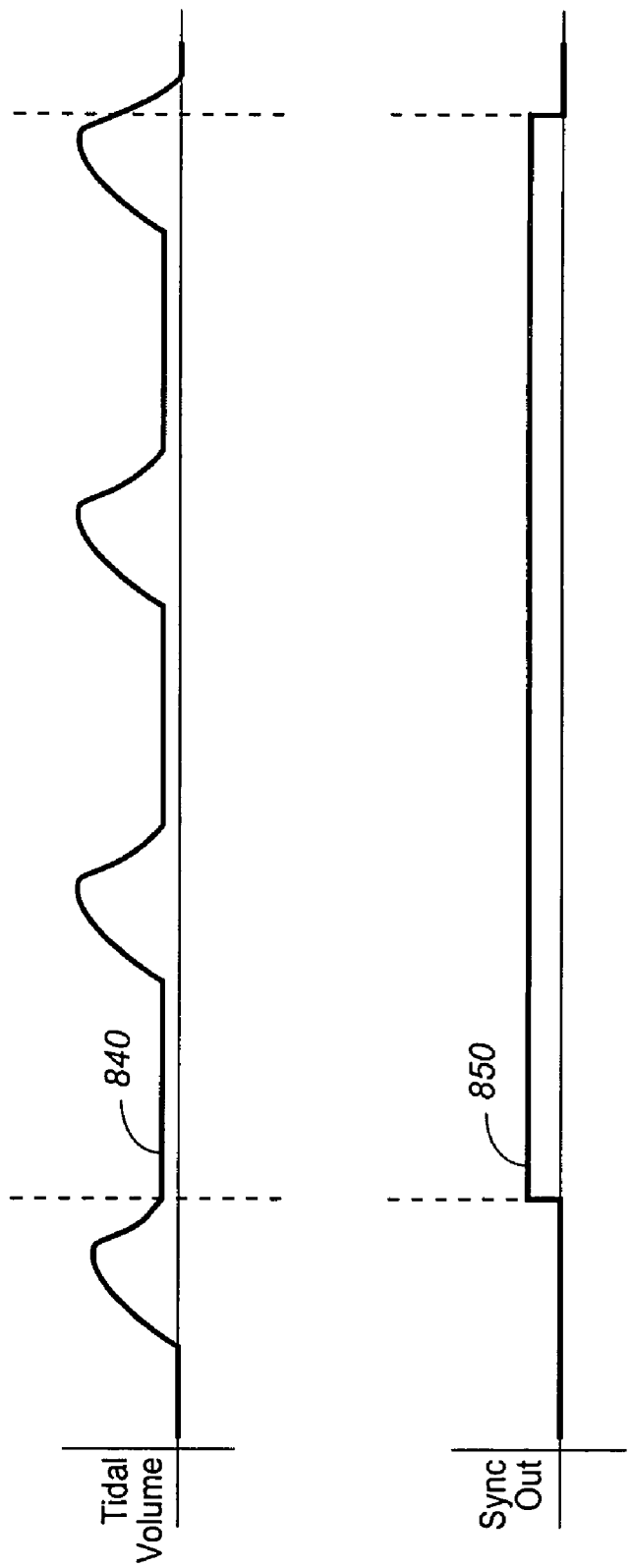
FIGS. 8A and 8B are schematic illustrations respectively of tidal volume and corresponding stimulation waveforms illustrating a stimulation method using a stimulation device in which stimulation is applied in accordance with the invention.

FIGS. 8A-8B illustrate stimulation and inspiration waveforms corresponding to a variation of a stimulation device and method or the invention. The stimulation protocol of FIG. 8B provides a low level of a continuous stimulation to cause the diaphragm to remain slightly contracted, thereby increasing functional residual capacity. FIG. 8B illustrates stimulation provided while FIG. 8A illustrates tidal volume. As shown, the tidal volume is elevated during the end portion of the exhalation cycle 840 (FIG. 8A) relative to end expiratory tidal volume before the stimulation.

Figure 9A:
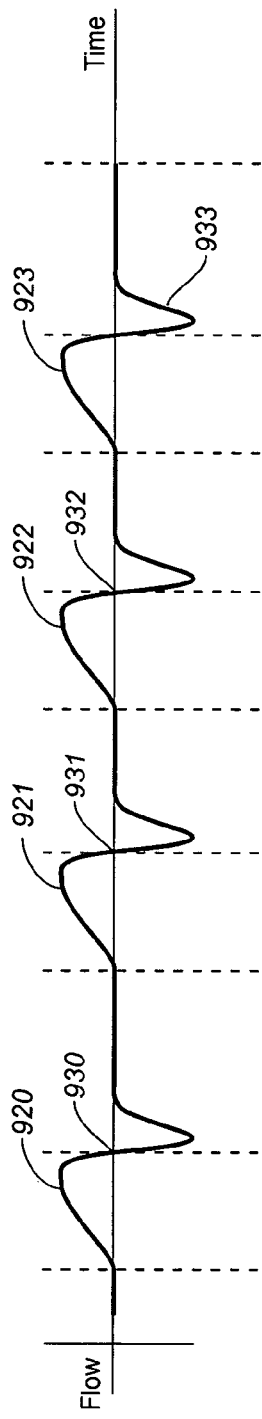
FIGS. 9A, 9B and 9C are schematic illustrations respectively of airflow, tidal volume and corresponding stimulation waveforms illustrating a stimulation method using a stimulation device in which stimulation is applied in accordance with the invention.
Figure 9B:
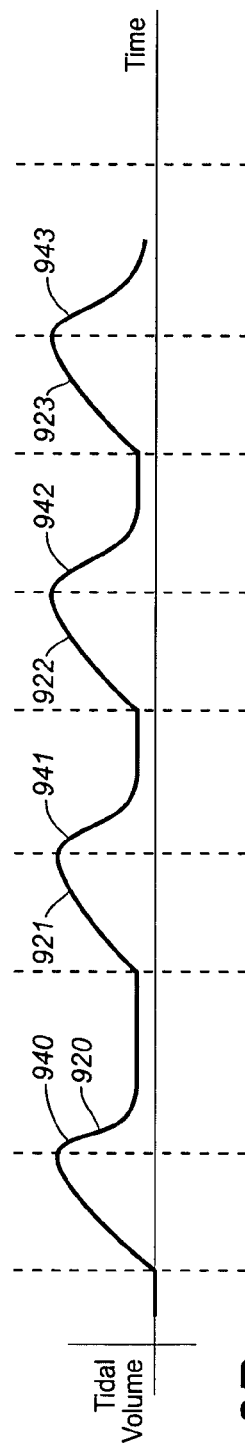
Figure 9C:
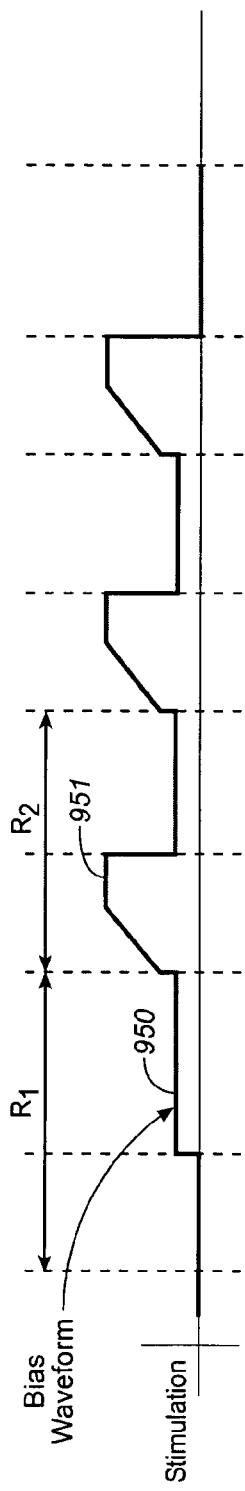

FIGS. 9A-9C illustrate stimulation and inspiration waveforms corresponding to a variation of a stimulation device and method of the invention. The stimulation protocol provides a combination of therapies or protocols including increasing functional residual capacity and controlling breathing. The stimulation protocols manipulate exhalation and control breathing. The stimulation protocol of FIGS. 9A-9C provides a low current stimulation 950 as shown in FIG. 9C during the exhalation phase of a respiration cycle and a stimulated breath 951 delivered at the end of exhalation. The stimulated breath 951 is provided at a higher rate R2 than the intrinsic rate R1. The stimulation 950 is applied between the end of inspiration cycles 920, 921, 922 and the onset of the next inspiration cycles, 921, 922, 923 respectively to increase functional residual capacity. Stimulation 951 produces inspiration cycles 920, 921, 922, 923. Flow waveforms 930, 931, 932, 933 respectively of respiration cycles 920, 921, 922, 923 are shown in FIG. 9A. Tidal volume waveforms 940, 941, 942, 943 respectively of respiration cycles 920, 921, 922, 923 are shown in FIG. 9B.

Figure 10A:
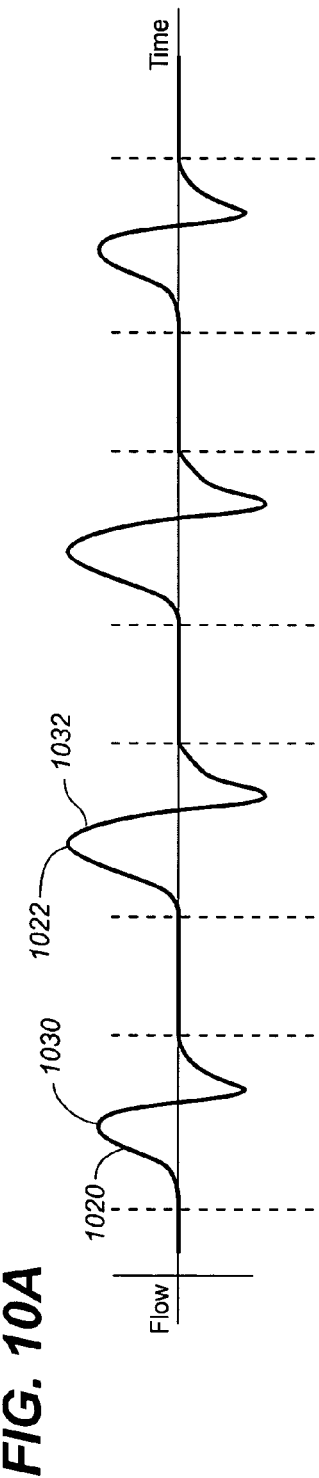
FIGS. 10A, 10B and 10C are schematic illustrations respectively of airflow, tidal volume and corresponding stimulation waveforms illustrating a stimulation method using a stimulation device in which stimulation is applied in accordance with the invention.
Figure 10B:
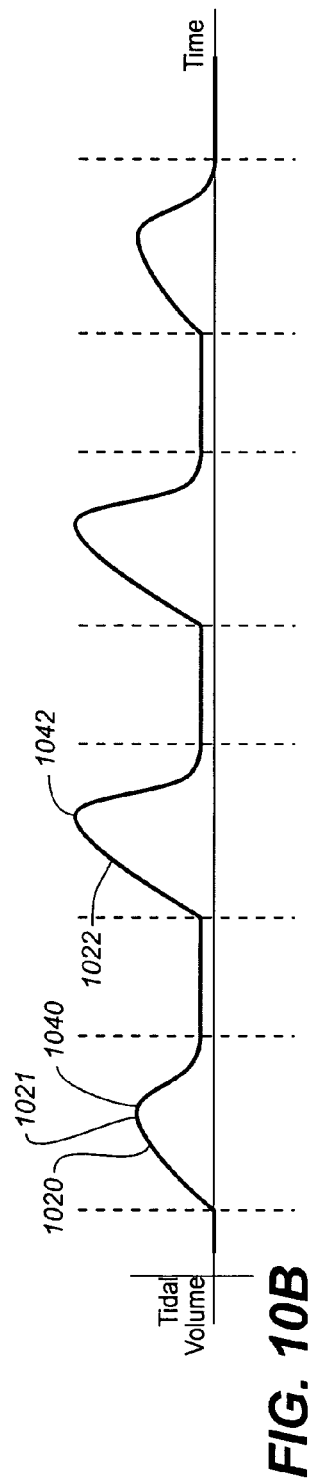
Figure 10C:
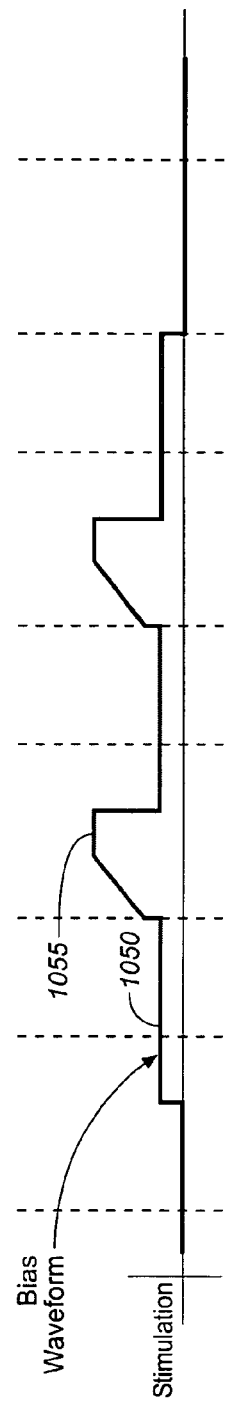

FIGS. 10A-10B illustrate stimulation and inspiration waveforms corresponding to a variation of a stimulation device and method of the invention. Stimulation is provided during the inspiration cycle in a manner shown in FIGS. 7A-7B to increase inspiration duration and tidal volume (with normalized peak flow) in order to stiffen the upper airway. Also, a low level stimulation is provided to increase lung capacity at the end of inspiration and until the beginning of the next inspiration cycle to increase the functional residual capacity. A first intrinsic respiration cycle 1020 is illustrated. At the onset of exhalation 1021 of the respiration cycle 1020, a low level stimulation 1050 is applied until the onset of the inspiration cycle of the next respiration cycle 1022. At the detection of the onset of the next respiration cycle 1022 (as described in FIGS. 16A-16D), stimulation 1055 is provided. The stimulation 1055 is applied at least in part during the inspiration cycle 1022. The corresponding tidal volumes 1040, 1042 of respiration cycles 1020, 1022 respectively are illustrated in FIG. 10A. The corresponding flows 1030, 1032 of respiration cycles 1020, 1022 respectively are shown in FIG. 10B.

Referring to FIGS. 11A and 11B, stimulation and inspiration waveforms illustrate a stimulation device and method of the invention. Stimulation is provided in a manner similar to that described with reference to FIGS. 4A-4D. In accordance with FIGS. 11A and 11B, stimulation is provided to prevent or mitigate obstructive sleep apnea by stabilizing the tidal volume. FIG. 11A schematically shows the tidal volume as sensed by EMG sensors and illustrates the intrinsic breathing 1111-1117 of a subject, as well as the resulting breathing 1124, 1125. FIG. 11B illustrates the stimulation pulse envelopes 1160 of stimulation applied to the diaphragm or phrenic nerve of a subject in accordance with one aspect of the invention. Referring to FIG. 11A, the tidal volume from intrinsic breathing gradually decreases (1111, 1112) until it falls below a threshold level 1150 (1113-1115) and then resumes normal tidal volume (1116-1117) after treatment. After breath 1113 is detected below threshold level 1150, a stimulation pulse 1160 is provided during and in synchronization with the subsequent breath 1114, 1115 to thereby provide the resulting breath. The resulting breaths have waveforms 1124, 1125 with tidal volumes increased to a level of normal breathing. According to one variation, stimulation is provided with the goal of stabilizing or normalizing breathing. After stimulating for a given period of time or number of breaths, breathing is monitored to determine if it is normalized (for example with breaths 1116, 1117) at which time the stimulation may be discontinued.

FIGS. 12A-12B illustrate stimulation and inspiration waveforms corresponding to a variation of a stimulation device and method of the invention. The stimulation protocol of FIGS. 12A-12B provides a long rising stimulation during at least the inspiration portion of a respiration cycle to increase inspiration time of the cycle with respect to expiration time(or total percentage of the cycle that corresponds to inspiration). Using breathing control therapy to lengthen the inspiratory duration, expiratory time is reduced and the baseline relaxation lung volume is not completely restored, leading to an increased functional residual capacity. The stimulation protocol thereby manipulates or shortens the length of the exhalation portion of the respiration cycle. In addition, the respiration rate is increased to shorten the exhalation portion of the respiration waveform. Thus, the protocol is directed to increasing the functional residual capacity of the lungs by manipulating the expiration phase of the respiration cycle.

FIG. 12A illustrates flow and FIG. 12B illustrates corresponding stimulation. Referring to FIG. 12A a first intrinsic breath 1210 is shown with an intrinsic inspiration volume $V_{II}$ and an intrinsic expiration volume $V_{IE}$. Prior to time $T_{12A}$, breathing may be entrained (for example, as described with respect to FIGS. 13A and 13B herein) at a rate slightly faster than the intrinsic rate but at approximately a normal tidal volume and waveform 1210. Thereafter, stimulation 1240 is applied during a rest period (i.e. at an end portion of the exhalation phase) of a respiration cycle 1220 following breath 1210. The stimulation is provided using a long rising pacing pulse so that the respiration cycle is lengthened by a time $T_{12B}$ to prevent full expiration before the next inspiration cycle of the next breath 1230 which is provided by stimulation 1250. Stimulation 1250 is provided at a rate slightly faster than the previous stimulation 1240. Thus, exhalation is shortened, preventing exhalation portion 1260, and thus increasing the functional residual capacity of the lungs.

Figures 13A, 13B:
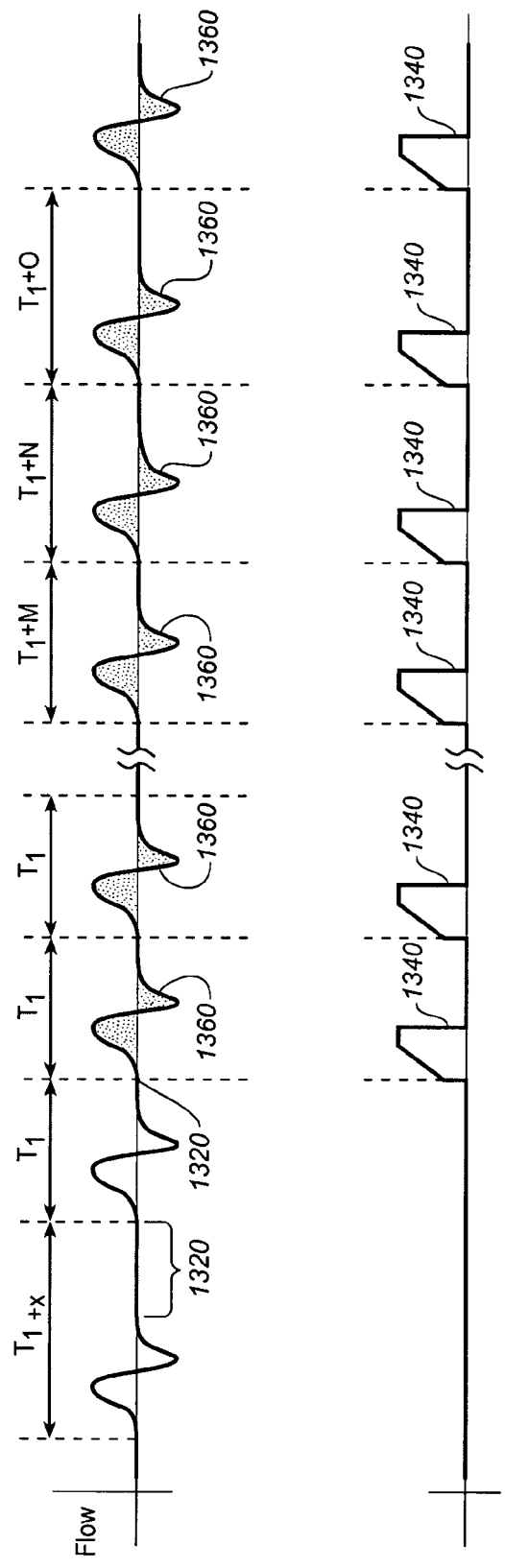
FIGS. 13A and 13B are schematic illustrations respectively of respiration response and stimulation waveforms illustrating a stimulation method using a stimulation device according to the invention.

Referring to FIGS. 13A-13B, stimulation and respiration waveforms illustrating a stimulation method using a stimulation device in accordance with one aspect of the invention are illustrated. According to FIGS. 13A-13B, breathing is stabilized by stimulating to control or manipulate breathing. FIGS. 13A-13B illustrate a variation of a technique for controlling breathing.

FIG. 13A illustrates the flow of air representing respiration waveforms over time. Breathing control may be used for a number of different purposes. It may be done with or without sensing a condition that indicates a respiratory disturbance is present or occurring. It may be done for a predetermined period of time or during certain times of day or during certain sleep cycles. It may be done to stabilize breathing.

For example, if tidal volume falls below a predetermined threshold, stimulation may begin. Stimulation may also be provided periodically or at times of greater vulnerability to obstructive sleep apnea or other disorders associated with breathing disorders. FIG. 13B illustrates envelopes 1340 of stimulation pulses provided to control breathing during the course of stimulation. FIG. 13A illustrates the breaths 1360 resulting from the stimulation illustrated in FIG. 13B.

According to this embodiment, the stimulator first takes over breathing by providing stimulation 1340 (as illustrated in FIG. 13B) at a time during an end portion 1320 of the exhalation phase of an intrinsic respiration cycle, prior to the onset of the next respiration cycle (As illustrated in FIG. 13A). The stimulation 1340 is provided at a rate greater than the intrinsic rate, i.e., where the cycle length T1 is less than the intrinsic cycle length T1+x. As illustrated the duration of the intrinsic respiration cycle is $T_1+x$. The duration of the respiration cycles of the stimulated breathing begins at $T_1$ to take over breathing. After a period of time of taking over breathing, the respiration cycle length is then gradually increased to T1+m, t1+n, and T1+o where m<n<o<x and where o approaches x in value. Breathing is thereby controlled and ventilation is accordingly stabilized.

According to one aspect of the invention, breathing is believed to be controlled by stimulating for a period of time at a rate greater than but close to the intrinsic respiratory rate. Breathing may be controlled through inhibition of the central respiratory drive or entrainment. In order to entrain breathing, stimulation may be provided until the central pattern generator activates the respiration mechanisms, which includes those of the upper airway, in phase with the stimulation through various feedback mechanisms. It is believed that breathing may be entrained when the central respiratory drive is conditioned to adapt to stimulation. When breathing is entrained, it may be possible to further slow respiration rate or the respiration cycle length so that it is longer than the intrinsic length 1320.

Some methods for controlling breathing are described for example in U.S. application Ser. No. 10/966,474, filed Oct. 15, 2004 and incorporated herein by reference.

Referring to FIGS. 14A and 14B inspiration flow waveforms and stimulation pulse envelope waveforms are shown corresponding to a variation of a stimulation device and method of the invention. In accordance with this variation, the stimulation device stimulates during intrinsic breaths 1411, 1412, 1413 to provide resulting breaths 1421, 1422, 1423. The intrinsic breaths occur at a rate B1 as illustrated in FIG. 14A. The first stimulation 1451 is applied at a delay D1 from the onset of intrinsic breath 1411. The next stimulation 1452 is provided at a delay D2 from the onset of intrinsic breath 1412 and the subsequent stimulation pulse 1453 is provided at a delay D3 from the onset of intrinsic breath 1413. The time between the first and second stimulation 1451 and 1452 is $T_{1+\Delta}$ a while the time between the second and third stimulation 1452 and 1453 is $T_1$, i.e., shorter. Thus stimulation is provided gradually closer and closer to the onset of stimulation to gently take over breathing with stimulation at least in part during intrinsic inspiration. The stimulation 1453 is essentially synchronous with the start of the intrinsic inspiration 1413, to create the resulting breath 1423. Stimulation may be delivered at this rate for a period of time. Then the next stimulus 1454 is delivered at a rate faster than normal at a respiration cycle length timed to thereby elicit paced breath 1424. The next stimulus 1455 is delivered at the interval T2, to induce another paced breath 1425, and this may be continued for some time in order to control breathing. This may lead to the entrainment of the central respiratory control system. Also, rate may be increased gradually until no intrinsic breaths occur between the paced breaths. When control of respiratory rate is achieved (and possibly entrainment), if a slowing of the breathing rate is desired, the pacing rate can be decreased gradually as shown schematically in the Figure by stimuli delivered at a cycle length of T2+x, followed by T2+2x, inducing paced breaths 1426 and 1427. It is believed that if entrained, if desired, the stimulation rate may bring the respiration rate slower than the intrinsic rate and tidal volume may be manipulated. After a period of time or after breathing has been controlled as desired, the intrinsic breathing may be allowed to resume, for example, as shown with breath 1418. The patient may be weaned off stimulation, for example, as described herein.

In accordance with another aspect of the invention, the phrenic nerve or diaphragm may be stimulated using the low level stimulation as described herein, through an OSA event after obstructive sleep apnea event has occurred The stimulation described or shown herein may be comprised of several stimulation parameters. For example a burst of pulses may form a square pulse envelope or may ramp up or down in amplitude or a combination thereof. The frequencies may vary or may be varied depending upon a desired result. In accordance with one embodiment, the burst frequency ranges between 5-500 Hz and more preferably between 20-50 Hz. However, other frequency ranges may be used as desired. Low level pulses or continuous stimulation may comprise stimulation at about 8 mA or less or may be determined on a case-by-case basis. However, other amplitudes and frequencies may be used as desired. The stimulation may be monophasic or may be biphasic. Stimulation may be provided in response to sensing respiration or other parameters. Alternatively, stimulation may be provided periodically or during specific times, for example during sleep, during sleep stage transitions, or during non-REM sleep.

Stimulation may also be slowly phased out. That is the patients may be weaned from stimulation slowly. In general, when paced breathing is ongoing, and the therapy is to be stopped, it may be beneficial to wean the patient off the therapy to avoid creating apnea that may lead to obstructions or arousals. Weaning off would involve a gradual decrease in rate, until an intrinsic breath is detected. Once an intrinsic breath is detected, the device would discontinue pacing and would return to monitoring mode. An example of a protocol for weaning a patient off from stimulation is described, for example, in U.S. application Ser. No. 10/686,891 filed Oct. 15, 2003. Other variations of weaning patients off are also possible.

Figure 15:
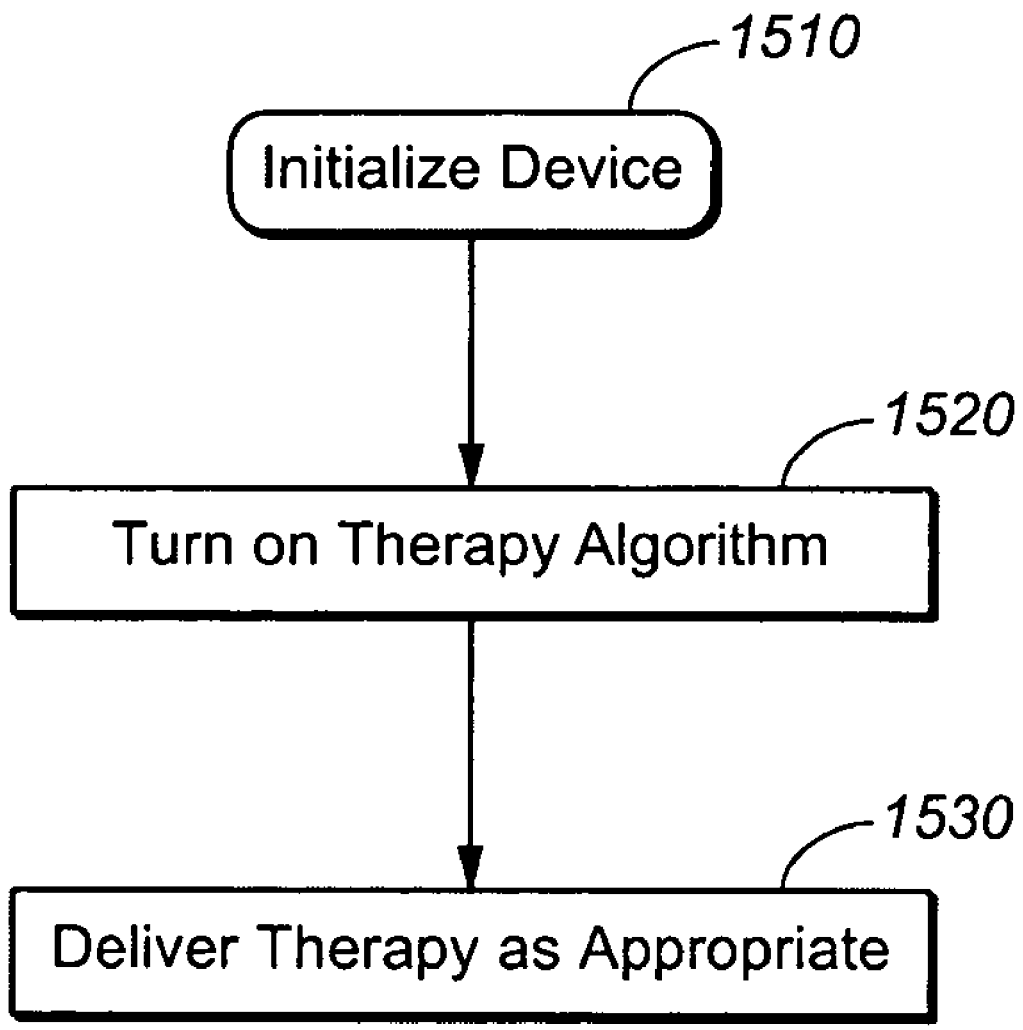
FIG. 15 is a flow chart illustrating operation of a device in accordance with the invention.

FIG. 15 is a flow chart illustrating operation of a system or device in accordance with the invention. An implanted device is initialized during an initialization period 1510. During the initialization period, among other things, the thresholds may be set up for triggering or inhibiting therapy. The thresholds may be set up by observing patient breathing over time. Therapy modalities may also be chosen, for example by testing various stimulation protocols to optimize therapy. For example, information obtained from one or more breaths can be used to set pacing parameters for subsequent therapies. Examples of data that can be obtained from one or a series of breaths include: rate, tidal volume, inspiration duration, flow parameters, peak flow, and/or duty-cycle. In the case of paced breathing therapies or breathing control (and possible entrainment), the rate of intrinsic breathing could be measured, and then paced breathing could be delivered, for example, at a faster rate than the measured rate. As another example, one could measure the inspiration duration of previous intrinsic breaths, and induce a breath to create an inspiration duration longer (or shorter) than the previous intrinsic breaths. During initialization or when updating the device, test stimulation signals and measured responses may be used to determine appropriate stimulation parameters.

During operation, the therapy is turned on 1520. This may be done automatically or manually. Therapy is delivered 1530 as is determined to be appropriate for a particular patient in accordance with one or more protocols, for example as described herein.

While the invention has been described with respect to treating obstructive sleep apnea, various aspects of the invention are not limited to use in obstructive sleep apnea patients.

The various techniques for controlling breathing as disclosed herein may be used in other therapeutic applications where controlling breathing is desired, for example in various breathing related disorders.

For example, stimulating breathing during intrinsic inspiration may be useful in any treatment involving control of breathing. Stimulating during intrinsic inspiration may be used as a technique to gradually begin to control or manipulate breathing parameters such as breathing rate, inspiration duration and tidal volume. Simulation during intrinsic breathing may be used with a number of breathing control protocols to initiate control of breathing, e.g., to gradually take over or to entrain breathing and to gradually control or manipulate breathing parameters.

The various techniques used to increase functional residual capacity maybe used in connection with any therapy where an increase in functional residual capacity results in a desired benefit.

Likewise, therapy described herein that stiffen the upper airway may also be used in any therapy for a breathing related disorder where the effects of improving upper airway patency are beneficial.

Similarly the techniques for controlling or entraining breathing as described herein may be used in other therapeutic applications where controlling or entraining breathing is desired.

Similarly, techniques for creating ventilatory stability as described herein may be used in other therapeutic application where stabilization is beneficial.

Stimulation may be provided at various times during sleep or various sleep stages or sleep transitions, including but not limited to, for example: prior to sleep, at sleep onset, upon detection of dropping tidal volume, upon detection of transition into REM or non-REM or during REM or non-REM sleep, or upon changes in breathing patterns, including but not limited to breathing rate.

The various stimulation protocols described herein may be combined in a variety of manners to achieve desired results.

The invention claimed is:

1. A method of manipulating breathing comprising:
   providing a stimulator programmed with an electrical stimulation protocol directed to improving ventilatory stability of a patient;
   sensing respiration via a sensor and identifying one or more portions of one or more respiratory cycles including first, second and subsequent intrinsic respiratory cycles by the patient detected internally within the patient's body;
   determining via a processor in communication with the sensor when the sensed respiration is a disordered event;
   when the disordered event is detected, applying electrical stimulation during a first selected intrinsic inspiration cycle at a first delay from an onset of the first intrinsic inspiration cycle;
   further applying the electrical stimulation during a second intrinsic inspiration cycle at a second delay from an onset of the second intrinsic cycle; and,
   further applying the electrical stimulation during one or more subsequent intrinsic breaths such that each stimulation is applied with a delay from an onset of each subsequent intrinsic breath such that the delay in each subsequent breath reduces from a previous delay until the stimulation is synchronous with a start of each subsequent intrinsic inspiration
   wherein the electrical stimulation is provided to tissue associated with the diaphragm of the patient at least in part during the intrinsic inspiration cycle in accordance with the electrical stimulation protocol until the sensed respiration has reached a normalized respiration such that ventilatory stability is improved.

2. The method of claim 1 wherein further applying the electrical stimulation during one or more subsequent intrinsic breaths comprises stimulating the tissue with the stimulator to provide a sequence of augmented intrinsic inspirations.

3. The method of claim 1 wherein further applying the electrical stimulation during one or more subsequent intrinsic breaths comprises providing multiple stimulations at a respiratory rate greater than or equal to an intrinsic respiratory rate.

4. The method of claim 1 wherein further applying the electrical stimulation during one or more subsequent intrinsic breaths comprises providing multiple stimulations configured to provide a minute ventilation approximately greater than or equal to an intrinsic minute ventilation.

5. The method of claim 1 wherein the identified one or more portions of the one or more respiratory cycles includes an exhalation portion, and the further applying the electrical stimulation during one or more subsequent intrinsic breaths comprises providing at least one of said plurality of stimulations during exhalation.

6. The method of claim 5 wherein the identified one or more portions of the one or more respiratory cycles includes a rest portion of an exhalation cycle, and the providing at least one of said plurality of stimulations during exhalation comprises stimulating during a rest phase portion of an exhalation cycle.

7. The method of claim 5 wherein providing at least one of said plurality of stimulations during exhalation comprises stimulating to elicit a breath during an exhalation cycle of an intrinsic respiration cycle.

8. A breathing stabilizer device for manipulating breathing comprising:
   an electrical stimulator programmed with an electrical stimulation protocol directed to controlling breathing of a patient;
   an electrode configured to be implanted to stimulate tissue associated with a phrenic nerve or diaphragm of a patient to cause a diaphragm response, wherein the stimulator is in electrical communication with the electrode to thereby supply an electrically stimulating signal to the tissue according to the electrical stimulation protocol;
   an intrinsic breathing detector configured to detect an intrinsic breath and to identify one or more portions of one or more respiratory cycles including an onset of a first, second and subsequent intrinsic breath internally within a patient's body; and
   a stimulation timer programmed to cause stimulation to occur during a respiratory cycle and to further stimulate breathing at a first respiratory rate greater than or equal to an intrinsic respiratory rate,
   wherein the stimulation timer is further programmed to initiate the stimulation upon detection of a respiratory disorder, where the stimulation is applied during a first selected intrinsic breath at a first delay from an onset of the first intrinsic breath, and where the stimulation is applied during a second intrinsic breath at a second delay from an onset of the second intrinsic breath such that the second delay is shorter than the first delay, and
   wherein the stimulation is further applied during one or more subsequent intrinsic breaths with each stimulation being applied at a delay from an onset of each subsequent intrinsic breath such that the delay in each subsequent intrinsic breath is shorter than a previous delay until the stimulation applied is synchronous with an onset of each subsequent intrinsic breath.

9. The device of claim 8 wherein the identified one or more portions of the one or more respiratory cycles includes an inspiration portion, and the stimulator is configured to provide stimulation during an inspiration portion of the intrinsic breaths.

10. The device of claim 9 wherein the stimulator is further configured to increase the rate of stimulation to a second respiratory rate after providing stimulation during the inspiration portion of the intrinsic breaths.

11. The device of claim 8 wherein the stimulator is programmed with an electrical stimulation protocol directed to entraining breathing of a patient.

12. The device of claim 8 wherein the identified one or more portions of the one or more respiratory cycles includes an exhalation portion, and the stimulator is further programmed to cause stimulation to occur during an exhalation portion of the respiratory cycles.

13. The device of claim 8 wherein the stimulator is configured to stimulate to elicit a sequence of augmented intrinsic inspirations.

14. The device of claim 8 wherein the stimulator is configured to entrain breathing with a sequence of a plurality of stimulations at respiratory rate greater than or equal to an intrinsic respiratory rate.

15. The device of claim 8 wherein the electrical stimulation protocol is further configured to approximately provide a sensed peak flow less than or equal to a peak flow of an intrinsic breath.

16. The device of claim 8 wherein the identified one or more portions of the one or more respiratory cycles includes an inspiration portion, and the stimulator is configured to apply the stimulation to occur at least in part during an inspiration portion of the intrinsic breaths of the patient.

* * * * *